United States Patent
Einarsson

(10) Patent No.: US 8,657,772 B2
(45) Date of Patent: Feb. 25, 2014

(54) WEARABLE DEVICE HAVING FEEDBACK CHARACTERISTICS

(75) Inventor: Palmi Einarsson, San Juan Capistrano, CA (US)

(73) Assignee: Össur hf., Reykjavik (IS)

( * ) Notice: Subject to any disclaimer, the term of this patent is extended or adjusted under 35 U.S.C. 154(b) by 904 days.

(21) Appl. No.: 12/175,548

(22) Filed: Jul. 18, 2008

(65) Prior Publication Data

US 2009/0024065 A1 Jan. 22, 2009

Related U.S. Application Data

(60) Provisional application No. 60/929,993, filed on Jul. 20, 2007.

(51) Int. Cl.
*A61F 5/00* (2006.01)

(52) U.S. Cl.
USPC .......... 602/23; 602/2; 602/26; 602/60; 482/8; 73/865.4

(58) Field of Classification Search
USPC ............. 602/2, 23, 26, 60–62; 600/386, 600/388–390; 482/5–8; 601/5, 33, 34; 73/1.37, 1.38, 1.75, 1.79, 865.4; 473/207, 215, 216, 266, 277; 33/511, 33/512; 2/78.1, 79, 227, 400, DIG. 3; 623/24, 44
See application file for complete search history.

(56) References Cited

U.S. PATENT DOCUMENTS

| 894,095 | A | 7/1908 | Anderson |
| 976,550 | A | 11/1910 | Coddington |
| 1,373,377 | A | 3/1921 | Albin |
| 1,490,265 | A | 4/1924 | Glasgow |

(Continued)

FOREIGN PATENT DOCUMENTS

| DE | 3438628 | 4/1986 |
| DE | 4014236 | 11/1991 |

(Continued)

OTHER PUBLICATIONS

Lori Rochelte Roniger, "Proprioceptive Deficits Predict Female Athlete Knee Injuries", In Stride With Sports Medicine, Jun. 2009, <www.biomech.com>.

(Continued)

*Primary Examiner* — Patricia Bianco
*Assistant Examiner* — Keri J Nelson
(74) *Attorney, Agent, or Firm* — Knobbe Martens Olson & Bear LLP

(57) ABSTRACT

A wearable device having feedback characteristics including a compliant article arranged to extend over an anatomical portion of a wearer and for providing a user with information regarding range of motion parameters of a joint and/or to condition users to maintain proper joint orientations. Sensors provided with the wearable device detect the orientation of the joint and send signals to a processor for analysis. When the processor determines that the joint is outside of predefined range of motion parameters or in an unsafe or potentially injurious configuration, a feedback or response mechanism is activated to alert the user to such a condition or to provide substantially rigid structural support to the joint. The sensors, processor, and feedback mechanisms can be provided in a monitoring and control package along a side of the compliant article.

28 Claims, 15 Drawing Sheets

(56) References Cited

U.S. PATENT DOCUMENTS

| | | | |
|---|---|---|---|
| 1,756,358 A | 4/1930 | Ingram |
| 1,983,829 A | 7/1933 | Ziminski |
| 2,332,119 A | 10/1943 | Springer |
| 2,606,551 A | 8/1952 | Piper |
| 2,778,358 A | 1/1957 | Keles |
| 2,843,116 A | 7/1958 | Grannan |
| 2,889,830 A | 6/1959 | Raymond |
| 3,351,053 A | 11/1967 | Stuttle |
| 3,605,731 A | 9/1971 | Tigges |
| 3,756,247 A | 9/1973 | Hand |
| 3,783,879 A | 1/1974 | Stalder |
| 3,989,041 A | 11/1976 | Davies |
| 4,426,884 A | 1/1984 | Polchaninoff |
| 4,481,941 A | 11/1984 | Rolfes |
| 4,576,154 A | 3/1986 | Hyman et al. |
| 4,696,291 A | 9/1987 | Tyo |
| 4,737,994 A * | 4/1988 | Galton ............ 2/465 |
| 4,790,855 A | 12/1988 | Jolly |
| 4,796,631 A | 1/1989 | Grigoryev |
| 4,829,994 A | 5/1989 | Kurth |
| 4,905,678 A | 3/1990 | Cumins et al. |
| 4,957,105 A | 9/1990 | Kurth |
| 4,964,628 A | 10/1990 | Poplawski |
| 4,977,893 A | 12/1990 | Hunt |
| 5,123,407 A | 6/1992 | Dewhurst |
| 5,128,655 A | 7/1992 | Shore |
| 5,143,092 A | 9/1992 | Flowers |
| 5,147,286 A | 9/1992 | Meals |
| 5,201,772 A | 4/1993 | Maxwell |
| 5,263,923 A | 11/1993 | Fujimoto |
| 5,267,928 A | 12/1993 | Barile et al. |
| 5,286,251 A | 2/1994 | Thompson et al. |
| 5,344,391 A | 9/1994 | Modglin |
| 5,368,552 A | 11/1994 | Williamson et al. |
| 5,383,920 A | 1/1995 | Sikes |
| 5,425,702 A | 6/1995 | Carn et al. |
| 5,449,002 A | 9/1995 | Goldman |
| 5,558,627 A | 9/1996 | Singer et al. |
| 5,620,412 A | 4/1997 | Modglin |
| 5,628,722 A | 5/1997 | Solomonow et al. |
| 5,662,123 A | 9/1997 | Goldman |
| 5,681,267 A | 10/1997 | Molino et al. |
| 5,718,672 A | 2/1998 | Woodman |
| 5,735,807 A | 4/1998 | Cropper |
| 5,754,121 A | 5/1998 | Ward et al. |
| 5,788,618 A | 8/1998 | Joutras |
| 5,814,001 A | 9/1998 | Schwenn et al. |
| 5,814,093 A | 9/1998 | Stein |
| 5,823,981 A | 10/1998 | Grim et al. |
| 5,827,209 A | 10/1998 | Gross |
| 5,840,050 A | 11/1998 | Lerman |
| D403,071 S | 12/1998 | Biedermann et al. |
| 5,843,007 A | 12/1998 | McEwen et al. |
| 5,893,367 A | 4/1999 | Dubats et al. |
| 5,895,366 A | 4/1999 | Bzoch |
| 5,928,175 A | 7/1999 | Tanaka |
| 5,947,913 A | 9/1999 | Palumbo |
| 5,968,002 A | 10/1999 | Morrisseau |
| 5,976,063 A | 11/1999 | Joutras et al. |
| 5,982,285 A | 11/1999 | Bueche et al. |
| 6,059,576 A * | 5/2000 | Brann ............ 434/247 |
| 6,119,516 A | 9/2000 | Hock |
| 6,129,689 A | 10/2000 | Dibello |
| 6,146,346 A | 11/2000 | Godwin |
| 6,149,690 A | 11/2000 | Belzidsky |
| 6,165,147 A | 12/2000 | Morrow |
| D439,343 S | 3/2001 | Kagan, II |
| 6,210,353 B1 | 4/2001 | Barnes |
| 6,270,469 B1 | 8/2001 | Mott |
| 6,319,216 B1 | 11/2001 | Coligado |
| 6,360,615 B1 | 3/2002 | Smela |
| 6,422,242 B1 | 7/2002 | Slautterback et al. |
| 6,436,058 B1 | 8/2002 | Krahner et al. |
| 6,494,853 B1 | 12/2002 | Rossi et al. |
| 6,540,703 B1 | 4/2003 | Lerman |
| 6,540,707 B1 | 4/2003 | Stark et al. |
| 6,544,202 B2 | 4/2003 | McEwen et al. |
| 6,579,248 B1 | 6/2003 | Cascone et al. |
| 6,592,539 B1 | 7/2003 | Einarsson et al. |
| 6,611,783 B2 | 8/2003 | Kelly, Jr. et al. |
| 6,622,719 B1 | 9/2003 | Slautterback et al. |
| 6,652,596 B2 | 11/2003 | Smith et al. |
| 6,740,057 B2 | 5/2004 | Grelsamer |
| 6,770,045 B2 | 8/2004 | Naft et al. |
| 6,852,067 B2 | 2/2005 | Limonadi |
| 6,872,187 B2 | 3/2005 | Stark et al. |
| 6,890,285 B2 | 5/2005 | Rahman et al. |
| 6,890,312 B1 | 5/2005 | Priester et al. |
| 6,969,365 B2 | 11/2005 | Scorvo |
| 7,017,195 B2 * | 3/2006 | Buckman et al. ............ 2/455 |
| 7,074,204 B2 | 7/2006 | Fujii et al. |
| 7,083,584 B2 | 8/2006 | Coligado |
| 7,087,031 B2 | 8/2006 | Rossi et al. |
| 7,101,487 B2 | 9/2006 | Hsu et al. |
| 7,131,998 B2 | 11/2006 | Pasolini |
| 7,150,048 B2 | 12/2006 | Buckman |
| 7,166,063 B2 | 1/2007 | Rahman et al. |
| 7,182,738 B2 | 2/2007 | Bonutti et al. |
| 7,210,240 B2 | 5/2007 | Townsend et al. |
| D559,393 S | 1/2008 | Schirrmacher |
| 7,377,944 B2 | 5/2008 | Janusson et al. |
| 7,396,337 B2 | 7/2008 | McBean et al. |
| 7,410,471 B1 | 8/2008 | Campbell et al. |
| 7,413,554 B2 | 8/2008 | Kobayashi et al. |
| 7,416,537 B1 | 8/2008 | Stark et al. |
| 7,416,538 B2 | 8/2008 | Katoh et al. |
| 7,425,171 B2 | 9/2008 | Maupin |
| 7,473,235 B2 | 1/2009 | Schwenn et al. |
| 7,476,185 B2 | 1/2009 | Drennan |
| 7,481,742 B2 | 1/2009 | Katoh et al. |
| 7,484,961 B2 | 2/2009 | Blaski et al. |
| 7,544,172 B2 | 6/2009 | Santos-Munne et al. |
| 7,552,021 B2 | 6/2009 | Bar-Haim et al. |
| 2001/0053884 A1 | 12/2001 | Krieg et al. |
| 2002/0082537 A1 | 6/2002 | MacAllister |
| 2003/0009120 A1 | 1/2003 | MacAllister |
| 2004/0010390 A1 | 1/2004 | Kelly, Jr. et al. |
| 2005/0126026 A1 * | 6/2005 | Townsend et al. ............ 33/512 |
| 2005/0203454 A1 | 9/2005 | Wiener |
| 2006/0015049 A1 | 1/2006 | Suarez et al. |
| 2006/0047232 A1 | 3/2006 | Bourne et al. |
| 2006/0074365 A1 | 4/2006 | Brown |
| 2006/0079824 A1 | 4/2006 | Munchl-Fals et al. |
| 2006/0142681 A1 | 6/2006 | Suarez et al. |
| 2006/0178605 A1 | 8/2006 | Sauber et al. |
| 2006/0258967 A1 | 11/2006 | Fujil et al. |
| 2006/0264790 A1 | 11/2006 | Kruijsen et al. |
| 2007/0027419 A1 | 2/2007 | Drennan |
| 2007/0043314 A1 | 2/2007 | Moore |
| 2007/0044196 A1 | 3/2007 | Wang |
| 2007/0055189 A1 | 3/2007 | Katoh et al. |
| 2007/0068512 A1 | 3/2007 | Chiang |
| 2007/0106190 A1 | 5/2007 | Katoh et al. |
| 2007/0149360 A1 | 6/2007 | Narayanaswami |
| 2007/0185425 A1 | 8/2007 | Einarsson et al. |
| 2007/0197945 A1 | 8/2007 | Islava |
| 2007/0287943 A1 | 12/2007 | Kendrick |
| 2008/0039756 A1 | 2/2008 | Thorsteinsson et al. |
| 2008/0132383 A1 * | 6/2008 | Einav et al. ............ 482/8 |
| 2008/0191864 A1 | 8/2008 | Wolfson |
| 2009/0088674 A1 | 4/2009 | Caillouette et al. |
| 2009/0137369 A1 | 5/2009 | Branch et al. |

FOREIGN PATENT DOCUMENTS

| | | |
|---|---|---|
| EP | 0 302 148 | 2/1989 |
| EP | 2070492 A1 | 6/2009 |
| WO | WO 0110508 | 2/2001 |
| WO | WO 2006/009970 | 1/2006 |
| WO | WO 2007/012068 | 1/2007 |
| WO | WO 2008/033013 | 3/2008 |
| WO | WO 2008/041614 | 4/2008 |

(56) References Cited

FOREIGN PATENT DOCUMENTS

OTHER PUBLICATIONS

Bledsoe Philippon Post-Op Hip Brace, <http://sportinjurysolutions.com/store/product19.html>.
POHB-1.jpg <http://www.footorthotics.co.uk/images/pictures/bodymedics/cervical->.
ROM-HIP.gif <http://www.orthopaedicsandtrauma.com/acatalog/rom-hip.gif>.
Inventables, Stretch Sensing Rubber <https://technology.inventables.com/technologies/stretch-sensing-rubber>.
Non-Invasive Sensors Design Kit, GlobalSpec, The Engineering Search Engine <http://www.globalspec.com/FeaturedProducts/Detail/Minco/NonInvasion . . . .
International Preliminary Report dated Feb. 4, 2010 in PCT/US2008/008775.

* cited by examiner

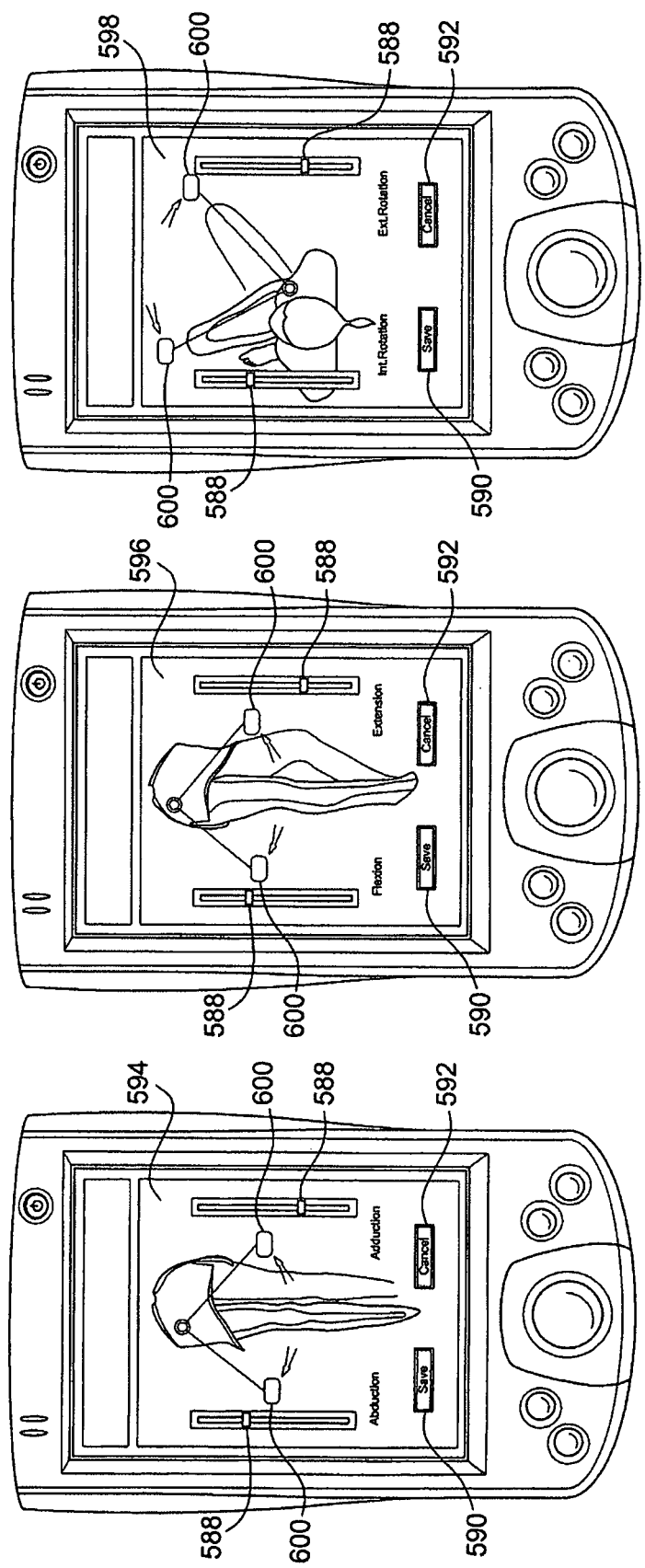

WEARABLE DEVICE HAVING FEEDBACK CHARACTERISTICS

This application claims the benefit of U.S. Provisional Application No. 60/929,993, filed Jul. 20, 2007.

FIELD OF THE INVENTION

The present invention relates generally to the field of wearable devices such as orthopedic and prosthetic devices, and more particularly to an orthopedic or prosthetic device that provides feedback to a user or practitioner when a set of conditions are near the extremes of acceptable ranges or outside of predefined norms.

BACKGROUND

Orthopedic braces are useful as preventative aids to prevent injuries to joints caused by motions or orientations of the joint that are outside the biomechanical limits of the joint. Orthopedic braces are also useful to promote proper healing of a joint following an injury to, or surgery on, the joint.

Knee braces in particular are widely used to treat a variety of knee infirmities. Such braces may be configured to impart forces or leverage on the limbs surrounding the knee joint in order to relieve compressive forces within a portion of the knee joint, or to reduce the load on that portion of the knee. Moreover, in the event that knee ligaments are weak and infirm, a knee brace may stabilize, protect, support, or rehabilitate the knee.

The knee is acknowledged as one of the weakest joints in the body, and serves as the articulating joint between the thigh and calf muscle groups. The knee is held together primarily by small but powerful ligaments. Knee instability arising out of cartilage damage, ligament strain and other causes is relatively commonplace since the knee joint is subjected to significant loads during the course of almost any kind of physical activity requiring the use of the legs.

Significantly, tearing of the ligaments in the knee also occur frequently, and typically require surgical intervention for proper healing to occur. According to the American Academy of Orthopeadic Surgeons (AAOS), over 80% of ligament injuries happen due to an excess rotation of the tibia with respect to the femur, thus causing the ligaments to tear. Most of these rotational injuries occur when an individual commences movement from a relaxed stance, or when a person is not utilizing or firing their muscles.

A limitation of existing orthopedic devices is that there are no devices that are readily available to effectively indicate to a user that such a potentially injurious situation exists. Thus, there is a need for a device that monitors joints and alerts a user when a joint is "out of phase" and is thus at risk of exposure to injury.

Rigid frame braces may be utilized to reduce the occurrence of such injuries by stabilizing a knee joint pre or post-surgery. However, there are numerous drawbacks to rigid frame braces. Such braces tend to be bulky and to add substantial weight to the user's leg. Further, rigid frame designs in ligament bracing tend reduce the performance of athletes, and a large number of physicians will not subscribe such ligament braces to their patients.

Additionally, the use of rigid frame braces in contact and incidental contact sports such as football, basketball, and soccer can lead to injuries to players coming into contact with a player wearing such a brace. Such injuries may include contusions, cuts, or even broken bones.

Further, a rigid frame brace is constantly rigid and constantly provides support to a joint, even when such support is unnecessary. The use of a rigid frame ligament brace on a leg to prevent injuries during activities is similar, in an extreme example, to inflating an air bag in a vehicle, attaching the seatbelt, and then attempting to drive the vehicle.

Thus, there is a need for an orthopedic device, such as a knee brace, for warning a user that a joint is "out of phase" and for preventing ligament and other tissue injury without reducing the performance of the wearer or duplicating other disadvantages of rigid frame brace designs. Such a device may be configured to be utilized to prevent injury to any joint of the body, including hip joints and the back. In a farther variation, the use of the warning system of such a device may be utilized in a manner to train a user and/or the user's muscles such that they maintain proper joint orientations to avoid injuries to the joint. In a farther variation, the use of a warning system may be used to condition amputees to utilize more effective and efficient biomechanical motions, for example, to achieve proper gait dynamics.

SUMMARY

A wearable device having feedback characteristics for training a user in proper biomechanical motions and/or joint orientations and/or for preventing injury to a joint is disclosed which maintains a feedback or response mechanism in an inactivated state during normal activities where the biomechanical motion of the joint is within predefined normal limits (norms), and which further activates the feedback or response mechanism once the biomechanical motion of the joint approaches the extremes of the acceptable predefined limits or is outside of the predefined limits.

Such a feedback or response mechanism may include any number of suitable devices or systems, such as selectively inflatable air cells, a shape memory material, a variable stiffness material, a variable viscosity fluid, providing a selective stimulus to a user, or any other suitable feedback or response mechanism.

The selective stimulus may be provided as electrical stimulation, as an electrical shock, as thermal variation, as a pulse, as vibration, as an audible and/or visual alarm, or as any other suitable stimulus to a user. The selective stimulus may be used alone or in combination with any other feedback or response mechanism. If the selective stimulus is used in combination with another feedback or response mechanism, the selective stimulus may be activated once the biomechanical motion of the joint is outside a first predefined norm range to alert the user of a potential injurious situation. Further, the additional feedback or response mechanism may be activated once the biomechanical motion of the joint is outside a second predefined norm range to prevent injury to the joint.

Such a device may be embodied in a compliant article arranged to extend over an anatomical portion of a wearer. The compliant article may be provided as a compression sleeve type knee brace. In order to detect the biomechanical motions of the joint, at least one sensor member is arranged on or within the compliant article. The sensor member may be configured to detect relative rotation between a tibia and a femur, and/or varus/valgus movements of a knee joint. An exemplary sensor may be an accelerometer or an inclinometer.

In order to utilize the sensor member and to activate the feedback or response mechanism, a processor is arranged to receive signals from the sensor member and to selectively send signals to the feedback or response element.

In an exemplary configuration, a wearable device in the form of a compliant article is provided having a feedback or response mechanism. The feedback or response mechanism is at least one air cell that extends in the proximal and distal direction along the compliant article and remains in the uninflated configuration when a detected condition is within predefined limits and achieves an inflated configuration when a detected condition is outside of the predefined limits such that the inflated air cell provides increased rigidity to the compliant brace. Further, a processor is arranged to receive signals from the sensor member and to selectively actuate a charge of compressed air to inflate the air cell.

In further exemplary configurations, a wearable device having feedback characteristics in the form of a compliant hip brace includes a monitoring and control package positioned along at least one side portion of the brace. The monitoring and control package includes appropriate sensors to monitor at least interior/exterior rotation, flexion and extension, and abduction and adduction of the hip joint. The monitoring and control package includes an internal power supply and processor for powering and reading signals provided by the sensors. The monitoring and control package also includes at least a display, and possibly other mechanisms, such as light emitting diodes (LEDs), audible alerts, or vibration mechanisms, to provide information and/or feedback to a user. In addition, the monitoring and control package includes either wired or wireless communication mechanisms to communicate with a remote monitoring and control module.

A user or practitioner can input range of motion ("ROM") settings into the remote monitoring and control module for programming the internal processor of the monitoring and control package of the hip brace. The range of motion parameters can be adjusted for various time frames to allow progressively larger ranges as time passes. A log can be stored in memory either by the internal processor or the remote monitoring and control module to provide a physician or practitioner with detailed information about the range of motion history for the user. When a user approaches or exceeds the preprogrammed range of motion for a particular parameter, the display and/or other mechanism can provide an alert to the user to indicate an unsafe condition.

The numerous advantages, features and functions of the various embodiments of a device providing feedback will become readily apparent and better understood in view of the following description and accompanying drawings. The following description is not intended to limit the scope of the device having feedback characteristics, but instead merely provides exemplary embodiments for ease of understanding.

BRIEF DESCRIPTION OF THE DRAWINGS

FIGS. 20-26 are various views showing input and output screens of a remote monitoring and control module for use with the variations of the device having feedback characteristics in the form of a hip brace shown in FIGS. 15 and 16.

Figure 1:
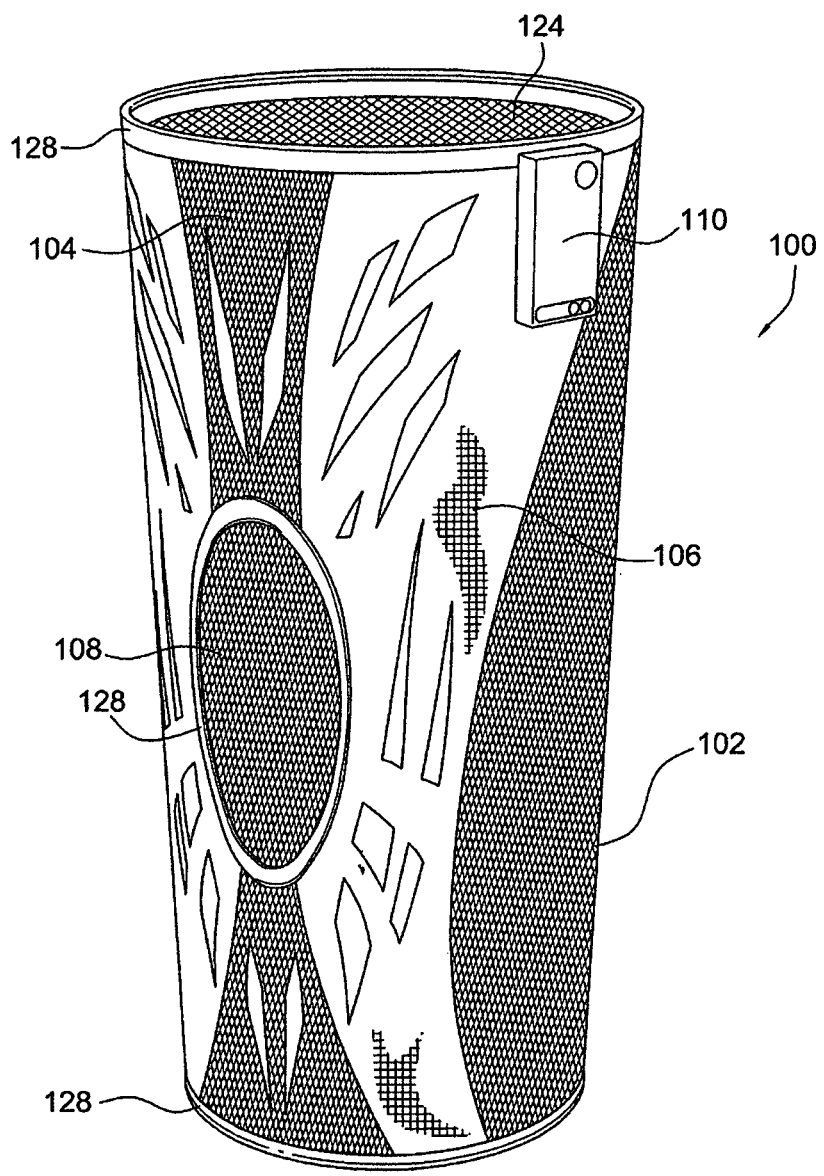
FIG. 1 is a front perspective view of one embodiment of a device having feedback characteristics according to the disclosure.

In the various figures, similar elements are provided with similar reference numbers. It should be noted that the drawing figures are not necessarily drawn to scale, but instead are drawn to provide a better understanding of the components thereof, and are not intended to be limiting in scope, but rather provide exemplary illustrations. It should also be noted that the features illustrated in a particular drawing may be utilized in an appropriate manner with any other suitable drawing figure. It should further be noted that the figures illustrate exemplary embodiments of a device having feedback characteristics, and in no way limit the structures or configurations of a device having feedback characteristics according to the present disclosure.

DETAILED DESCRIPTION OF VARIOUS EMBODIMENTS

A. Environment and Context of the Various Embodiments

A wearable device having feedback characteristics for use in training a user and/or a user's muscles in proper biomechanical motions and joint orientations and/or for use in preventing injuries to joints is described herein. Such a device may be exemplarily embodied in a lightweight, compliant, brace that provides maximal support to the joint when such support is needed, such as immediately prior to an injurious movement of the joint, in contrast to a rigid frame brace, which provides maximal support to a joint at all times, even when such support is unnecessary. Thus, the device having feedback characteristics is a streamlined device that provides maximal support to the joint when such support is necessary, and not constant maximal support. Of course, it is also contemplated that the features of the disclosed devices having feedback characteristics may also be used in conjunction with a rigid or semi-rigid frame brace in order to train users of such a brace in proper biomechanical motions.

Warning systems may be provided in the device to alert the user of an unsafe condition that may lead to an injury and/or the impending activation of a feedback or response mechanism. Such a warning system may be utilized to train the user and/or the user's muscles in the proper orientations of the joint in order to avoid injuries. Such a warning system may also be utilized to condition an amputee to utilize more efficient biomechanical motions, for example, to achieve proper gait dynamics.

While the device having feedback characteristics will be described herein with particular reference to the knee joint, the device is not limited to use with a knee joint. Any joint that is subject to injury due to biomechanical motions that extend beyond normal limits may benefit from the use of a device having feedback characteristics as described herein. For example, a device having feedback characteristics may be utilized with ankle, elbow, wrist, hip, or shoulder joints, the back, or any other joint in the body. In particular, variations of a device having feedback characteristics in the form of a compliant hip brace are discussed herein.

Figure 14:
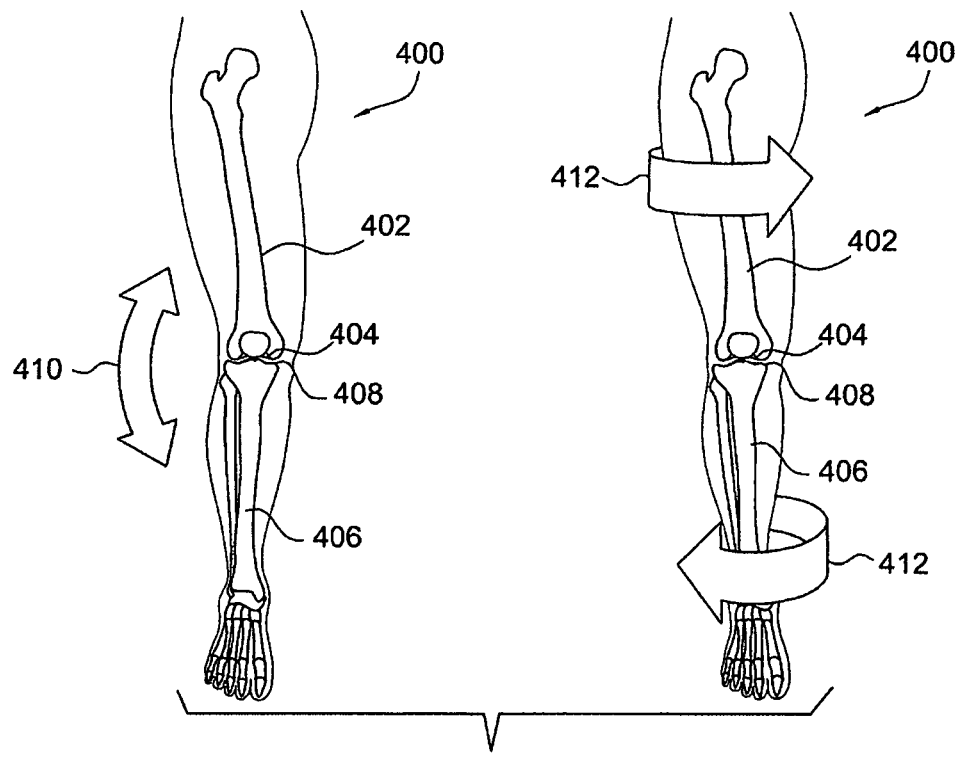
FIG. 14 is a diagrammatical view of the varus/valgus movement of the knee and relative rotation between the femur and tibia of the leg.

Referring to FIG. 14, a diagrammatic illustration of a leg 400 is provided. As can be seen, the upper or proximal portion of the leg 400 includes a femur bone 402, which has a femoral condyle 404 formed at its distal end. Similarly, the lower portion of the leg 400 includes a tibia bone 406, which has a tibial plateau 408 formed at its proximal end. The femoral condyle and the tibial plateau 404, 408 form the basis of the knee joint, along with the patella bone (not shown) and the numerous muscles and ligaments that form the connections and motive elements of the knee joint.

As previously mentioned, a large number of ligament tears occur due to the relative rotation 412 between the femur and the tibia of the leg. While the knee joint is typically designed to allow for a minute amount of such rotation 412 without causing damage to the joint, excessive amounts of such rotation 412 can tear the ligaments of the knee joint.

Additionally, excessive varus/valgus motion 410, which describes the amount of bowing (varus) of the knee or a knock-knee (valgus) condition, can be the source of injuries to the knee joint. Again, while the knee joint will typically tolerate some varus/valgus motion 410, excessive varus/valgus motion 410 will cause injury to the knee joint.

Accordingly, there are acceptable ranges of tibial-femoral rotation and varus/valgus notion, within which such rotation or motion will not cause immediate injury to the knee joint. Such acceptable ranges may be generalized for the public as a whole, but may vary from individual to individual, depending upon any number of factors. Additionally, such ranges may vary with a particular individual in a time frame following an injury or surgery. Exemplary factors include, but are not limited to, the age of the person, existing joint degradation, such as previous injuries to the joint or a post-surgery joint, and ligament strength. There is also more likelihood of injury to the joint where a person begins movement from a rest position when the orientation of the joint is near the extremes of the acceptable ranges, or is outside of the acceptable ranges.

The device having feedback characteristics in a preferred embodiment, exemplified herein as a knee brace, functions in this environment to provide increased support to a joint only when the increased support is necessary, instead of at all times. Additionally, the device having feedback characteristics may provide notification to a user when the joint is approaching or is in an out of norm orientation. The warning system may be used in physical therapy or exercise regimens to train the user and/or the muscles of the particular joint to maintain the joint in proper orientations to avoid potential injuries.

For further ease of understanding the device having feedback characteristics as disclosed herein, a description of a few terms is necessary. As used herein, the term "frameless" refers to a device that does not utilize a rigid or semi-rigid support to reinforce the anatomy. Additionally, the term "compliant" has its ordinary meaning and refers to an item that is able to adapt, or conform, its shape to a shape of another article. Further, the term "proximal" has its ordinary meaning and refers to a location that is closer to the heart than another location. Likewise, the term "distal" has its ordinary meaning and refers to a location that is farther from the heart than another location. The term "lateral" further has its ordinary meaning and refers to a location lying at or extending toward the right or left side, away from the median axis of the body. Additionally, the term "medial" has its ordinary meaning and refers to a location lying or extending toward the median axis of the body. The term "posterior" also has its ordinary meaning and refers to a location that is behind or to the rear of another location. Lastly, the term "anterior" has its ordinary meaning and refers to a location that is ahead of or to the front of another location.

Figure 2:
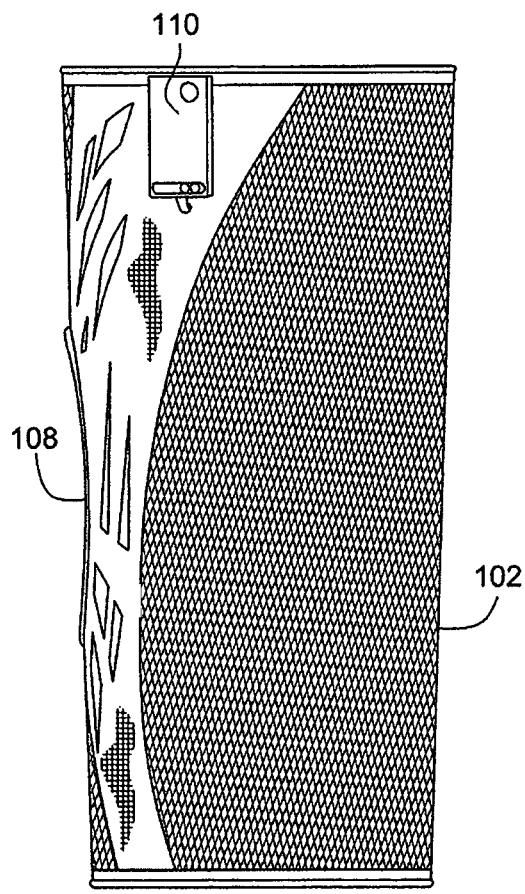
FIG. 2 is a side view of the device of FIG. 1.
Figure 3:
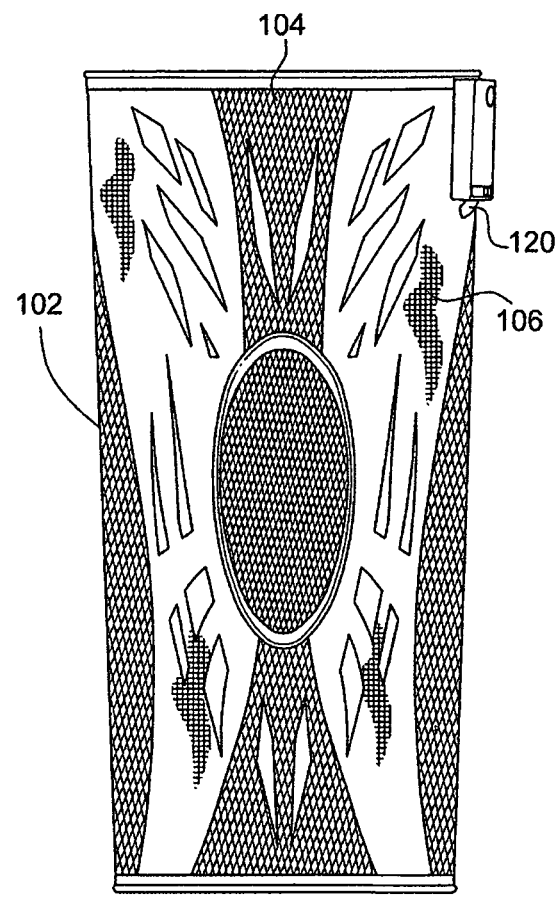
FIG. 3 is a front view of the device of FIG. 1.

B. Detailed Description of a Wearable Device Having Feedback Characteristics in the Form of a Knee Brace Referring to FIGS. 1-3, an embodiment of a wearable device having feedback characteristics is illustrated in the form of a knee brace 100. As shown in the illustrated exemplary embodiment, the brace 100 is preferably a frameless, compliant, tubular shaped sleeve open at the proximal and distal ends so that a user can slide the brace over the leg in order to situate the brace over the knee. The sleeve is slightly larger in circumference at the proximal end than the distal end in order to accommodate the larger dimension of the lower and/or upper thigh as compared to the upper and/or lower calf and shin. It will be recognized that additional semi-rigid or rigid support frames may be utilized in conjunction with the brace 100.

In the illustrated exemplary embodiment, the brace 100 is preferably a frameless compression type brace that provides minimal support to the knee due to the compliance and elasticity of the materials that form the brace. Exemplary configurations and materials for such compressive braces are described in U.S. Pat. No. 6,592,539, granted Jul. 15, 2003, and U.S. Pat. No. 5,823,981, granted Oct. 20, 1998, and both herein incorporated by reference.

The brace 100 includes an outer cover 102 that defines an opening or clearance 108 in the anterior portion of the brace for the patella bone of the knee. The opening 108 thus allows the remainder of the brace 100 to more closely conform to the leg and knee joint to maximize the amount of the support provided by the compliant brace. The outer cover 102 may be formed from a compliant, highly breathable spacer fabric 104, with patches of abrasion resistant fabric 106 in appropriate locations. Exemplary highly breathable spacer fabrics are described in U.S. patent application Ser. No. 11/723,604, filed Mar. 21, 2007, published as publication no. 2007/0185425 on Aug. 9, 2007, and herein incorporated by reference.

In order to aid with maintaining the brace 100 in position on the joint, stabilizing features may be used. An example of such stabilizing features includes breathable silicone strips 124 which are attached at the proximal and distal open ends of the brace 100. The strips 124 provide a tacky surface that will stick to the skin to prevent the brace 100 from sliding up and down the leg. Since the strips 124 are breathable, perspiration is drawn away to further reduce any slippage of the brace on the leg. The strips 124 may be attached in any known manner, such as adhesive or sewing. Exemplary configurations and materials for such breathable silicone strips are described in U.S. patent application publication no. 2007/0185425, published Aug. 9, 2007, and herein incorporated by reference.

Figure 4:
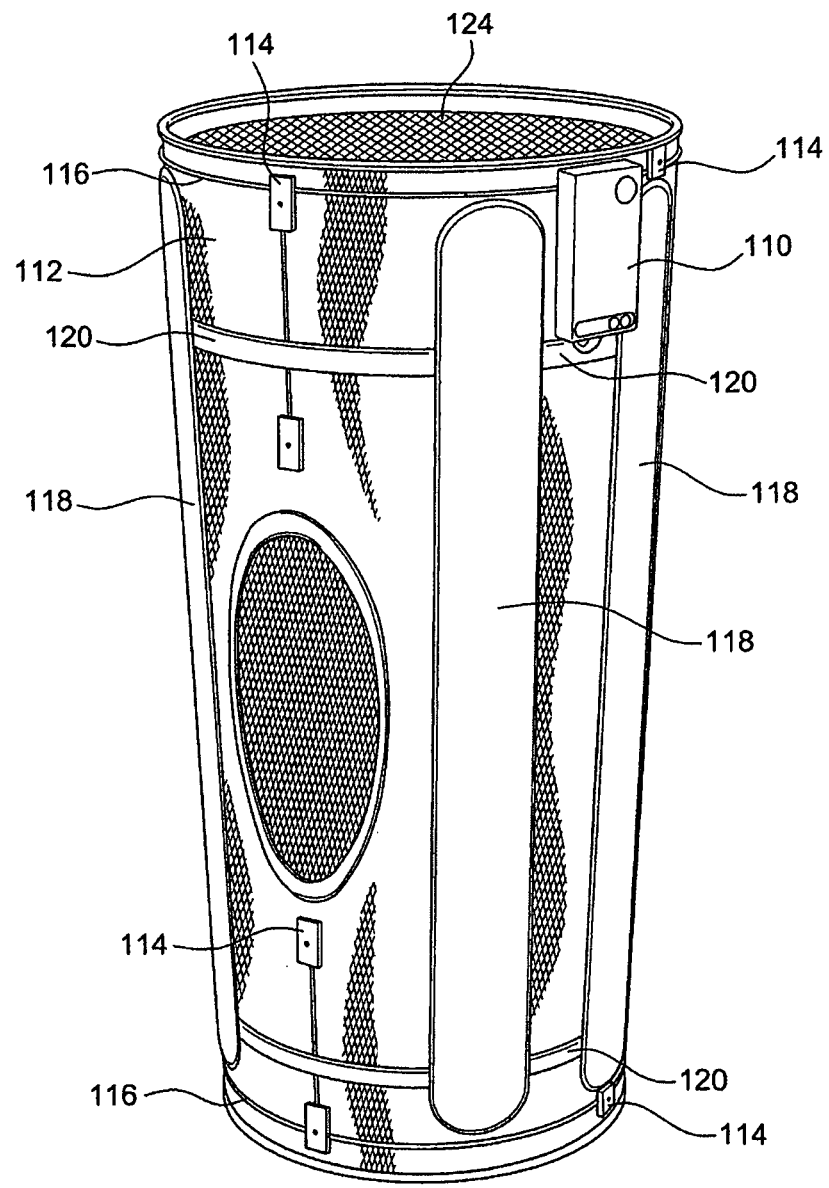
FIG. 4 is a front perspective view of the inner cover of the device of FIG. 1.
Figure 11:
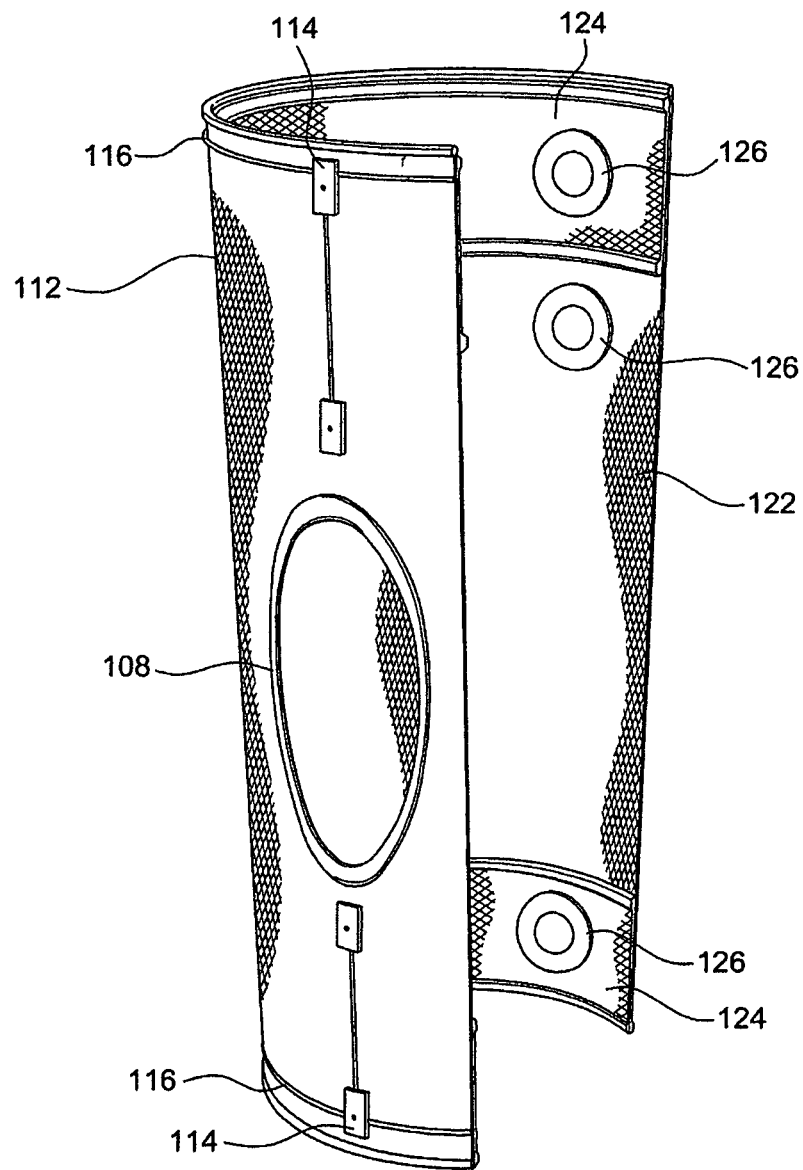
FIG. 11 is a perspective sectional view of another embodiment of an inner cover for a device having feedback characteristics.

Referring to FIGS. 4 and 11, the strips 124 are mounted to an inner surface 122 of an inner cover 112 of the brace. The inner cover 112 is received within the outer cover 102 to form a sleeve type compression brace. A clearance hole 108 to allow the patella bone of a knee joint to extend therethrough passes coincidentally through the outer and inner covers 102, 112. Thus, the remaining portions of the sleeves will more closely conform to the joint to provide a secure fit for the brace.

Referring again to FIGS. 1-3, the inner cover 112 and the outer cover 102 are attached to each other at the proximal and distal ends, and around the patella clearance hole 108 via seams 128. The seams may be formed in any suitable manner, such as by sewing, heat sealing, sonic welding, or any other suitable manner which will allow the inner cover 112 and the outer cover 102 to be attached to each other.

When the inner cover 112 and the outer cover 102 are attached to each other, a space is formed between them. This space is enclosed and minimized due to the elastic properties of the inner cover 112 and the outer cover 102. Thus, the outer cover 102 substantially conforms to the shape of the inner cover 112. It is noted that the device having feedback characteristics may also be embodied in a single tubular sleeve that is not built up from inner and outer covers.

Figure 5:
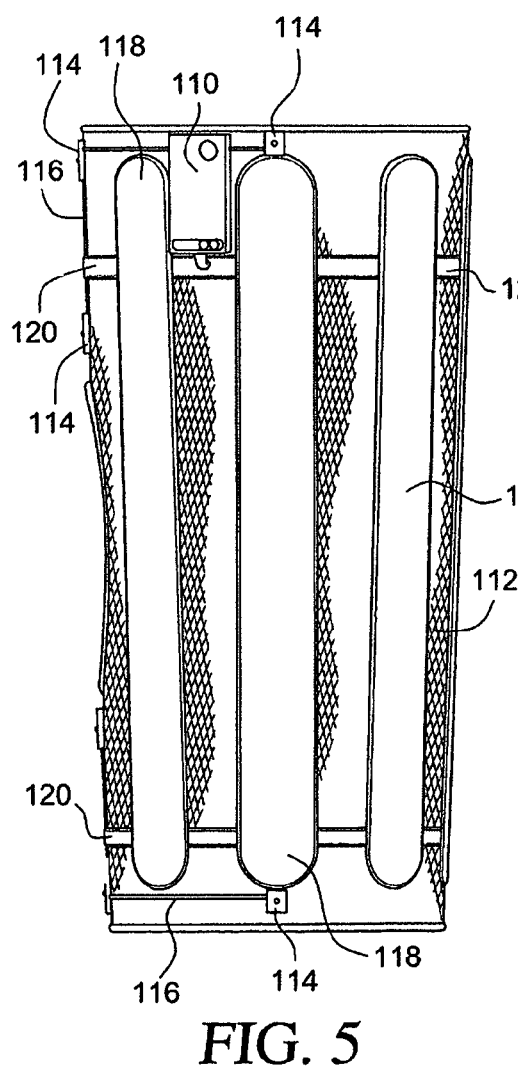
FIG. 5 is a side view of the inner cover of the device of FIG. 1.
Figure 6:
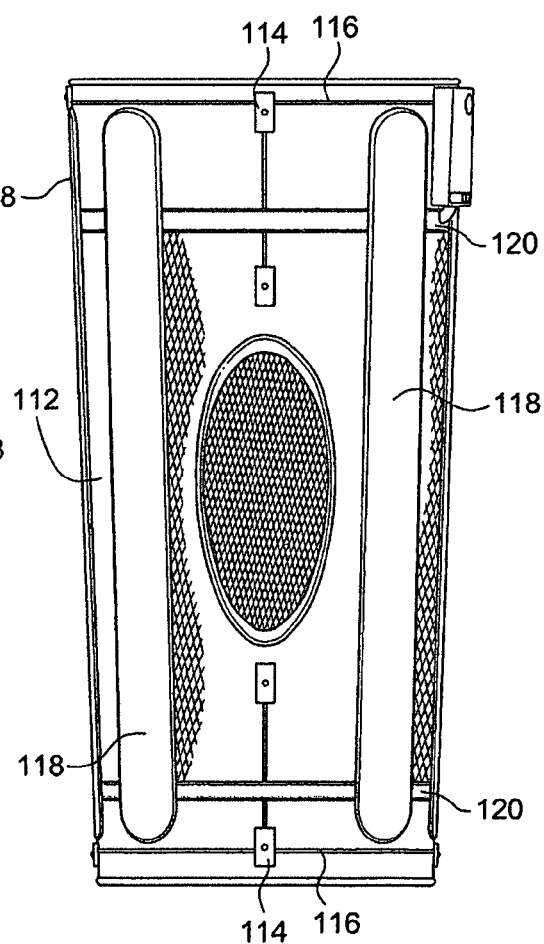
FIG. 6 is a front view of the inner cover of the device of FIG. 1.

As illustrated in FIGS. 4-6, the inner cover 112 is shown separately from the outer cover 102. The inner workings of an exemplary configuration of a device having feedback characteristics are shown in an inactive configuration.

In this embodiment, air cells or air bags 118 provide a feedback mechanism. The air cells 118 are positioned in a spaced relationship around the outer circumference of the inner cover 112. For example, an air cell 118 is positioned at each 45° interval around the outer periphery of the inner cover 112, with the exception of the interval that spans the patella clearance hole 108. Of course, any suitable number of air cells may be provided in any suitable configuration, such as one air cell positioned at each 60° interval around the tubular sleeve. Alternative configurations may include intervals of 30°, or intervals of 90°. Of course, any desired interval may be used.

The air cells 118 are positioned within the space between the inner and outer covers, and are thus hidden from view. The air cells 118 are oriented in substantially axially alignment with the sleeve along the proximal and distal direction. In this manner, the air cells 118 extend along and past both the femoral condyle and the tibial plateau of the knee joint.

Fluid passages 120 extend circumferentially around the sleeve and provide a fluid connection between each of the air cells 118. The fluid passages are positioned near the proximal and distal ends of the sleeve such that each air cell 118 is fluidically connected to the neighboring air cells 118 near the proximal and distal ends of each air cell 118. In this manner, when it is desired to activate, or inflate, the air cells 118, a quicker inflation can be achieved. Of course, only a proximal or a distal set of passages 120 may be provided, for example, to aid with ease of manufacturing or assembly.

The assembly of passages 120 and air cells 118 may be loosely received within the space between the inner and outer covers 112, 102. The seams 128 between the inner and outer covers 112, 102 will retain the assembly between the inner and outer covers 112, 102. However, additional attachment of the air cells 118 to the inner 112 and/or outer 102 covers may be desirable to prevent shifting of the assembly within the space between the inner and outer covers 112, 102.

The air cells 118 may be attached to the inner 112 and/or outer 102 covers in any suitable manner. For example, an adhesive may be used to adhere a respective portion of each air cell to the inner 112 and/or outer 102 covers. Since the inner and outer covers 112, 102 are compliant, one half of each air cell 118 may be adhered to the inner cover 112, and the other half may be adhered to the outer cover 102. Of course, any suitable portion of each air cell 118, such as one-quarter, or one-third, may be adhered to each of the inner and outer covers 112, 102. Other suitable methods of attaching the air cells to the inner and outer covers 112, 102 may also include sewing, heat sealing, ultrasonic welding, or any other suitable method. Additionally, the air cells may be removably attached utilizing hook and loop type fasteners, snap fasteners, zippers, or any other suitable releasable attachment system.

As discussed above, and as will be discussed in greater detail below, the air cells 118 may be selectively activated, or inflated. To accomplish the activation, a control box 110 is provided. The control box 110 includes a fluid connection passage 120 that communicates with the other fluid connection passages 120. The control box 110 may be mounted to the outer cover 102 with the passage 120 extending therethrough. The control box 110 may be mounted in any suitable manner, such as by an adhesive or by threads engaging eyelets on the control box.

In a variation, the control box 110 may be mounted to the inner cover 112 in a similar fashion. The outer cover 102 may have a cut-out portion or other accommodating structure to receive the control box 110. Further, the control box may be removably attached in any manner previously discussed. In a further variation, the control box may be remotely positioned from the device having feedback characteristics, for example on a wrist, arm, ankle, or head band. In such a variation, the control box may communicate with sensors through wires, or may be a wireless connection, including, but not limited to, infrared signals, radio frequency (RF) signals, or other conventional methods such as Bluetooth.

The control box also communicates with sensors 114 through electrical communication lines or wires 116 which may be incorporated into the material of the inner or outer cover, or may simply be adhered to the surface of the inner or outer cover. Alternatively, any type of wireless connection may also be used. The sensors 114 may be accelerometers, inclinometers, strain gauges, or any other suitable sensing device that can sense or detect various motions, conditions, or positions of the knee joint. The sensors may be mounted using any of the aforementioned mounting and removable attachment techniques. The sensors 114 may be mounted at specified locations around the periphery of the inner cover 112.

Figure 7:
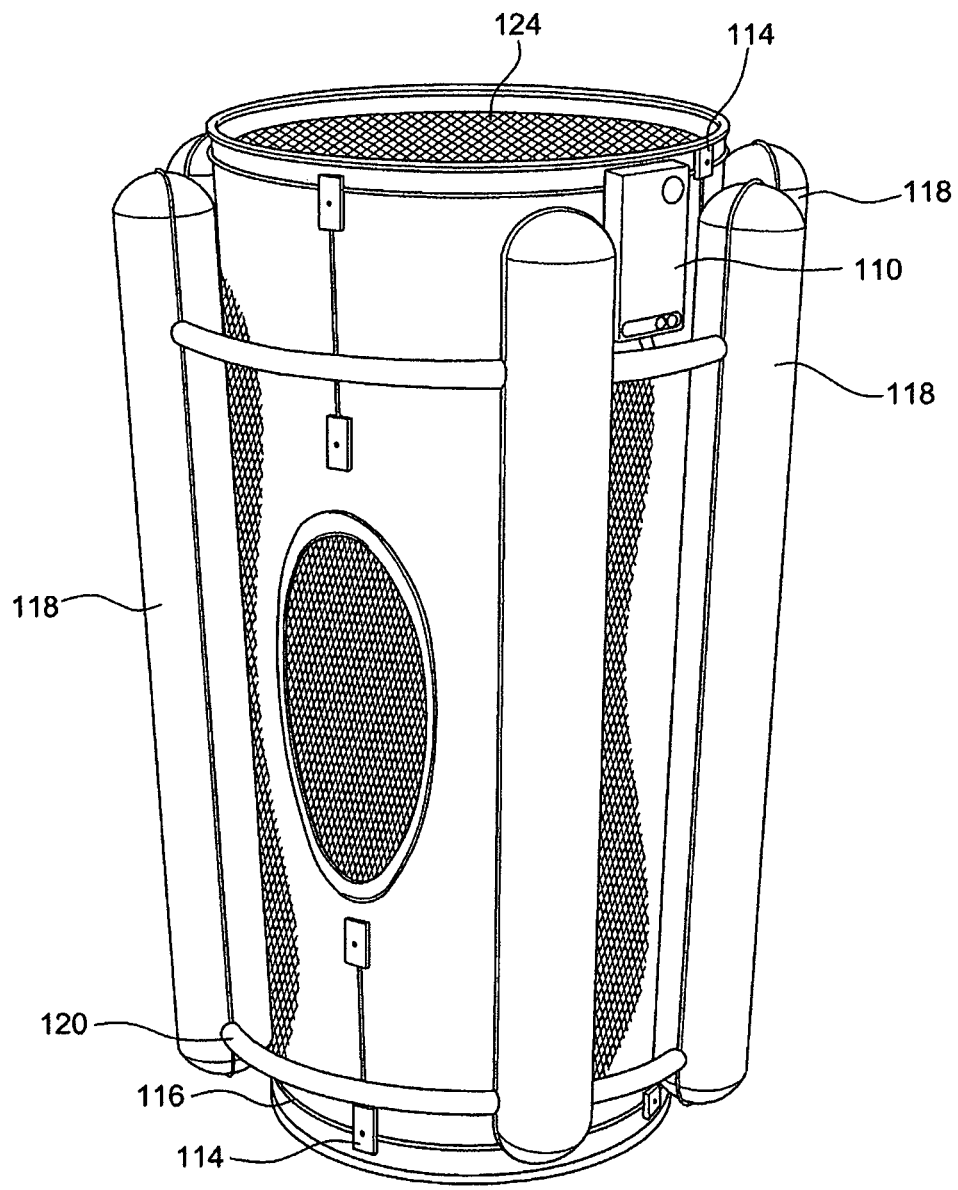
FIG. 7 is a front perspective view of the inner cover of the device of FIG. 1 with the air cells inflated.

For example, as illustrated in FIG. 7, sensors 114 may be mounted at 90° intervals around the circumference of the inner cover at the anterior, lateral, and medial sides, although any desired configuration or interval may be used. Multiple sensors 114 are mounted axially along the anterior side of the inner cover 112 around the patella clearance hole 108. Measuring motions, accelerations, and/or angles around the patella provides a more accurate picture of the condition or orientation of the knee, since the bones, cartilage, and ligaments of the knee all come together in this area to define the knee joint.

The sensors 114 communicate the sensed information or conditions to a processor within the control box 110, which utilizes the transmitted information to determine whether or when to activate and inflate the air cells 118. The sensors 114 may be configured to sense conditions of the knee joint, such as the amount of varus/valgus motion and the relative rotation between the femur and the tibia. If the sensors 114 are accelerometers, the detected accelerations may be converted into positional information in a recognized manner. Additionally, if the sensors 114 are accelerometers, the sensed condition may simply be the accelerations at the points where the sensors 114 are attached.

Figures 8, 9:
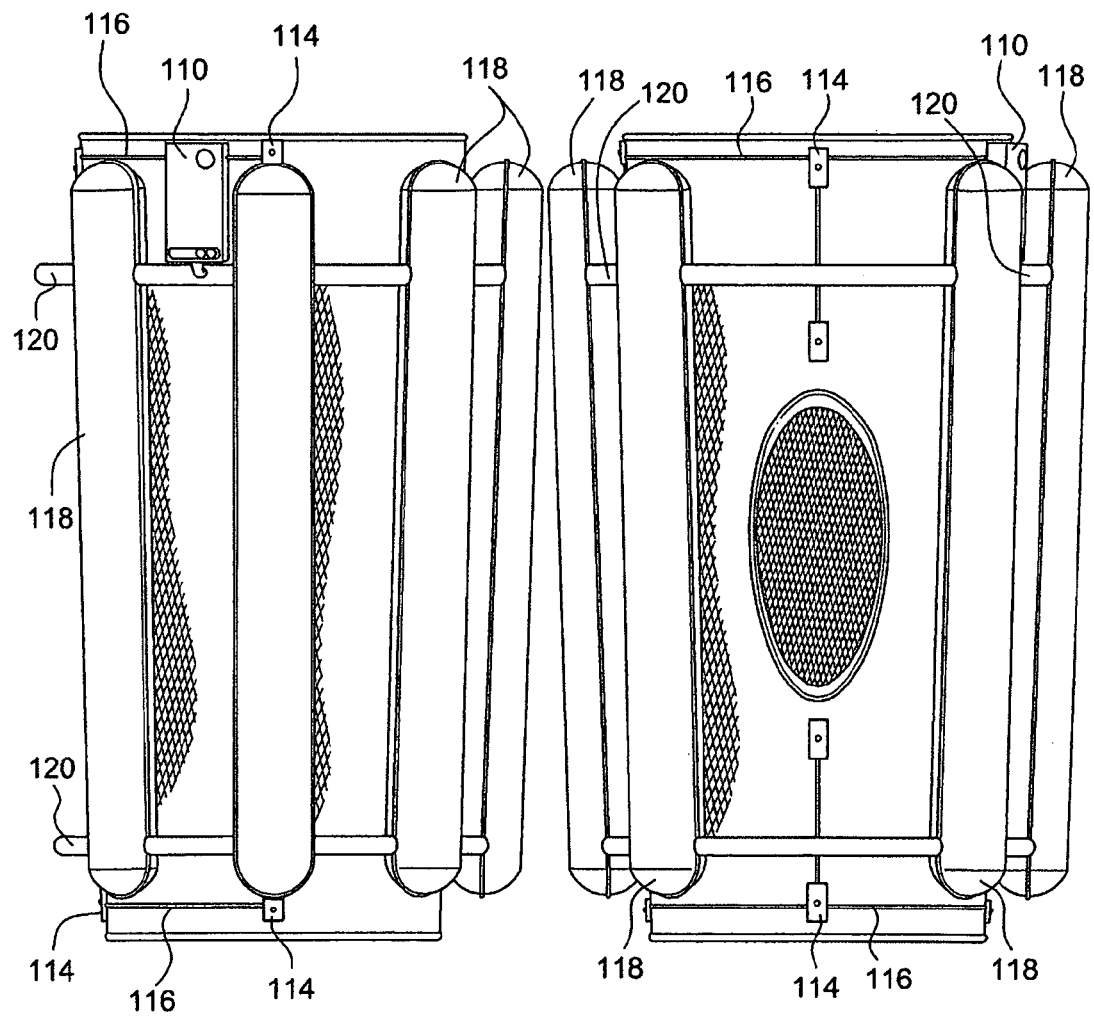
FIG. 8 is a side view of the inner cover of the device of FIG. 1 with the air cells inflated.
FIG. 9 is a front view of the inner cover of the device of FIG. 1 with the air cells inflated.

Referring to FIGS. 7-9, the wearable device having feedback characteristics is shown with the air cells 118 in an activated or inflated condition. Once the air cells 118 are inflated, they act as substantially rigid supports to prevent undesired orientations or the undesired motion of the joint in order to prevent injuries, such as torn ligaments. While one inflated air cell on its own may be compressed or bent and the covers 112, 102 are individually compliant, the combination of the inflated air cells 118 and the inner and outer covers 112, 102 together provide a substantially rigid brace to prevent injury to the joint.

Figure 10:
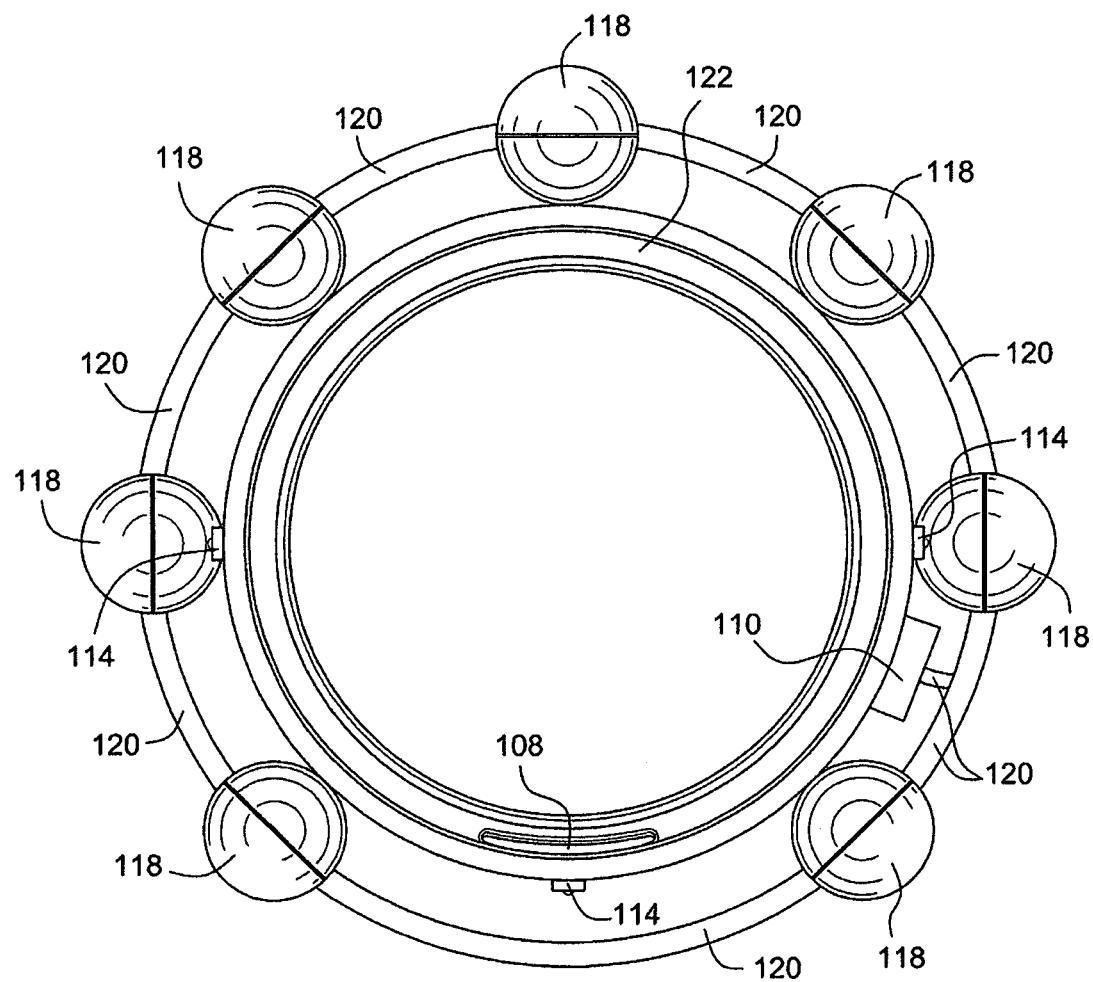
FIG. 10 is a top down view of the inner cover of the device of FIG. 1 with the air cells inflated.

As illustrated in FIG. 10, the air cells 118 are positioned around the outer circumference of the inner cover 112 in substantially equal increments. No air cell is provided over the patella, for the same reason that the patella clearance hole 108 is provided, the fit of the brace would be reduced if an air cell were to be positioned over the patella and inflated.

The air cells 118 that are provided have a low profile when in an inactivated or uninflated state, thus traditional disadvantages of bulky rigid braces are avoided. Further, when the air cells 118 are activated or inflated, they act as a substantially rigid cage to protect the knee joint.

Thus, in the inactivated state, the exemplary knee brace 100 preferably has no rigid components to provide support to the knee joint. Thus, the cumbersome and uncomfortable rigid supports that are typical of orthopedic braces are eliminated. However, when an injurious condition arises, the knee brace 100 can instantly respond by inflating the air cells 118 in order to provide a substantially rigid brace at the needed time. Thus, a brace is provided that is rigid only when absolutely necessary, and is compliant for the remainder of the time it is used, in contrast to a brace that is constantly rigid at all times. Of course, it will be recognized that additional semi-rigid or rigid supports can be utilized in combination with the exemplary knee brace 100.

In reference to FIG. 11, in a variation of the wearable device having feedback characteristics, electrical stimuli elements 126 are utilized. These electrical stimuli elements 126 may be used as the sole feedback or response mechanism, as illustrated. Alternatively, the electrical stimuli elements 126 may be used in combination with other feedback or response mechanisms, such as the previously described air cells.

The electrical stimuli 126 are positioned at appropriate locations on the inner cover 112 such that they are in contact with the skin of a wearer. The electrical stimuli 126 may be electrodes to provide electrical stimulation to the muscles of the user, in which case the locations of the electrical stimuli 126 on the inner cover 112 are determined by the location of the muscles around the joint.

The electrical stimuli 126 may also be electrodes to provide a pulse or a shock to the user to indicate that the joint is in an unsafe or unstable position and that the occurrence of an injury is likely. In any configuration, the electrical stimuli 126 and the device having feedback characteristics may be used in physical therapy or exercise regimens to train the user or their muscles in the proper orientations of the joint and to avoid injuries by alerting the user that the joint is out of phase or otherwise approaching an unsafe orientation. In this manner, through conditioning the user will remember proper joint orientations and the muscle memory will retain information on proper joint orientations. Thus, the device having feedback characteristics may be utilized to train users, as well as to prevent injuries to joints.

As previously noted, the electrical stimuli 126 may also be used in conjunction with air cells 118. In such a configuration, the electrical stimuli 126 may be utilized to warn the user of an impending injurious situation, for example when the joint is near the extremes of the range for normal conditions, and the air cells 118 may be used to prevent an injury once the thresholds of the range for normal conditions have been approached or broken.

Figure 12:
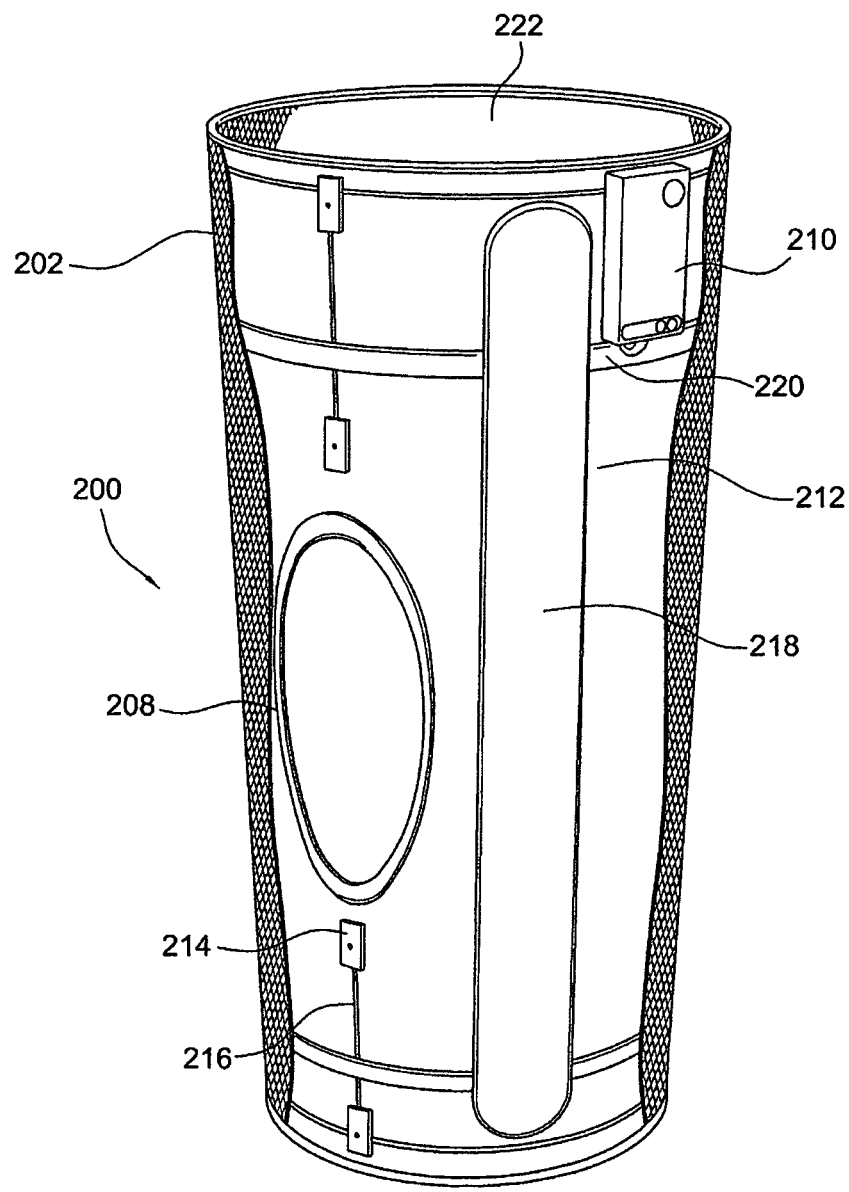
FIG. 12 is a perspective cut-away view of yet another embodiment of a device having feedback characteristics.

In another variation, referring to FIG. 12, a wearable device having feedback characteristics 200 includes an outer cover 202 that has a uniform surface or material. A patella clearance hole 208 extends through the outer cover 202 and coincidentally through an inner cover 212. The inner cover 212 has a uniform inner surface 222 that does not include strips of silicone material at the distal and proximal ends. Alternatively, a silicone coating may be provided over a portion of or the entire inner surface 222. The use of such uniform inner and outer covers allows the device having feedback characteristics to be more easily manufactured, with fewer steps and materials.

The construction of this embodiment is similar to the previously described embodiments. The inner cover 212 and the outer cover 202 are attached to each other and define a space therebetween. Sensors 214, electrical wires 216, air cells 218, and fluid passages 220 are all positioned in the space between the inner and outer covers 212, 202. A control box 210 is attached to either the inner or the outer cover 212, 202.

The exemplary wearable device having feedback characteristics 200 is again a compression sleeve type knee brace that provides little structural support while the air cells 218 are inactivated, and that provides a substantially rigid brace once the air cells 218 are activated. Thus, as previously described, a low profile, compliant, lightweight brace can be transformed into a substantially rigid brace nearly instantaneously.

Figure 13:
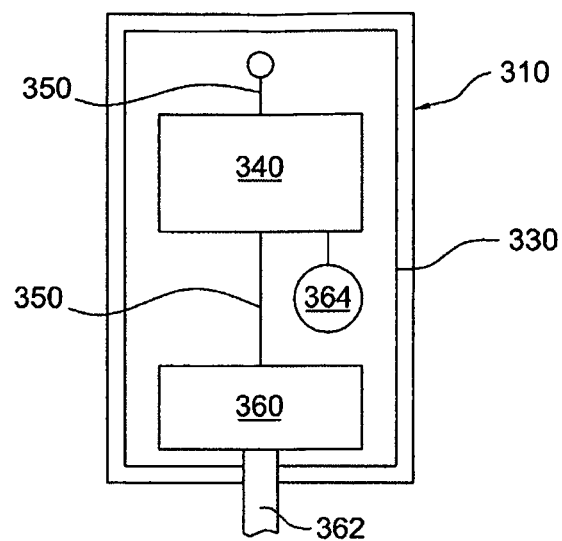
FIG. 13 is a diagrammatical view of an exemplary control box for use with a device having feedback characteristics.

C. Detailed Description of a Control Box for Use with a Wearable Device Having Feedback Characteristics In reference to FIG. 13, an exemplary control box 310 for use with a device having feedback characteristics includes a circuit board 330 or other substrate that allows the connection of elements thereto in electrical communication with each other.

A processor 340, as has been previously mentioned, is attached to the circuit board 330. The processor is electrically connected to sensors (not shown) via leads 350. The processor is also electrically connected to a battery 364 (battery herein may be any configuration of a single or multiple batteries, single or multiple cell batteries, alkaline and/or rechargeable batteries of any type, or any other suitable power source) and a compressed air charge 360 via leads 350. The leads 350 may be drawn on the circuit board 330 in a manner that will be recognized. The battery 364 and the compressed air charge 360 are also connected to the circuit board 330.

The compressed air charge 360 may be any known device for producing or exhausting compressed air in response to a signal from the processor 340. For example, the compressed air charge may be a canister of compressed air having a release valve that is actuated by the processor 340. Alternatively, the compressed air charge may be a chemical charge that releases compressed air when actuated by an electrical signal from the processor 340. The compressed air leaves the control box 310 via the fluid connection 362, which is connected to air cells in a manner previously discussed.

It will be recognized that if air cells are not utilized, the compressed air charge will not be necessary.

It is noted that the components of the control box may be mounted directly to the device having feedback characteristics in any suitable manner without the use of a control box. For example, each component of the control box may be directly mounted to the inner or outer covers described above and connected via insulated wires in a known manner, without the use of a circuit board.

As previously mentioned, the control box may be remotely located with respect to the device having feedback characteristics, such as, for example, on a wrist band or armband, to provide easier access thereto. Such access may be for the purposes of replacing a battery, a compressed air charge, or other component thereof. Remote location of the control box may also allow the positioning of the control box in a more protected location, or a location that is more isolated from jarring vibrations.

D. Description of the Functions of a Wearable Device Having Feedback Characteristics Having described exemplary configurations of a wearable device having feedback characteristics in the form of frameless, compression type knee braces, the associated exemplary functions are now described.

Referring again to the embodiments of FIGS. 1-10, and 12, the device having feedback characteristics 100 includes sensors (accelerometers) 114, selectively inflatable air cells 118, and a processor (within the control box 110). The processor is programmed with information and procedures to receive information from the sensors and activate (inflate) the selectively inflatable air cells at an appropriate time. In other variations, the processor can be programmed to activate the other feedback mechanisms and stimuli.

The processor may be programmed with no initial settings or factory default settings, which may be modified by a practitioner as needed. For example, a remote programming and control module may be connected to the processor through electrical wires or in any suitable wireless manner. The remote programming and control module can be utilized to send signals to the processor to modify and alter the programmed ranges and activation thresholds.

Such a control module may be useful to allow a practitioner to control the degree of motion of a joint, for example, flexion, extension, adduction, and abduction to allow a physical therapy training regimen to be implemented with a patient. For example, the device having feedback characteristics may be utilized post-surgery to aid with the recovery of an injured joint. For example, in the first week following such a surgery, the practitioner may wish to provide for only minimal motion of the joint, and the device having feedback characteristics can be programmed accordingly. In successive days or weeks, the processor can be reprogrammed, utilizing the control module, to allow for increasing ranges of motions. Thus, the allowable motion of the joint may be incrementally increased to allow for proper healing of the joint. Further, should setbacks be encountered, the ranges of acceptable motions may be decreased to provide additional time for recovery.

In an exemplary embodiment, the processor is programmed with an array of acceptable ranges for the orientations of the joint. For example, in reference to varus/valgus motion, the acceptable range of motion may be 5° in each direction. In reference to relative rotation between the tibia and femur, the acceptable range of motion may also be 5° in each direction. These ranges are provided for discussion purposes only since, as previously noted, the acceptable ranges will depend upon many conditions and may vary from user to user, or may vary within a single user.

Accordingly, the acceptable ranges are programmed into the processor in any suitable manner such that the processor can make determinations of whether the signals received from the sensors indicate that an injury is likely or imminent.

The processor is also programmed with information on the relative positions of the sensors, and algorithms to convert the electrical signals from the sensors into information regarding the orientation of the joint. The use of appropriate algorithms is determined based upon the type of sensors used and the positions of the sensors.

The sensors communicate with the processor by sending signals that indicate sensed conditions, such as accelerations in particular directions, of the joint. The processor receives the signals from the sensors and analyzes the signals to determine the orientation of the joint.

The detected orientation of the joint is compared to the stored acceptable ranges for the orientation of the joint. The comparison of the orientations may be expressed as a percentage of the detected orientation with respect to the acceptable range. For example, if the detected orientation of the joint is 0° of varus/valgus motion and is 0° of relative tibial/femoral rotation (the zero point of the range), the percentage may be expressed as 0%. Any motions that deviate from the zero point may be expressed as a positive percentage.

The processor is programmed to leave the air cells unactivated (uninflated) until a potentially injurious orientation of the joint is detected. The particular orientation that triggers the processor to activate (inflate) the air cells may be any desired orientation. For example, the processor may be programmed to inflate the air cells once the detected orientation of the joint is outside of the programmed acceptable ranges. In terms of the percentage example discussed above, once the detected range exceeds 100% it is outside the acceptable ranges.

Alternatively, the processor may be programmed to inflate the air cells once the detected orientation of the joint is near the extremes of the programmed acceptable ranges. In terms of the percentage example discussed above, once the detected range exceeds 95%, for example, it may be considered to be near the extremes of the acceptable ranges. Of course, the determination of the detected orientation is near the extremes of the acceptable ranges may vary from user to user or based upon the condition of the joint.

In any of the above described cases, once the processor detects the potentially injurious orientation of the joint, the processor sends a signal or otherwise activates the air cells. As discussed above, a charge of compressed air is released upon the signal from the processor to inflate the air cells. The total inflation of the air cells may occur in a matter of microseconds, such that the time between when a potentially injurious orientation is detected and when the air cells are activated is quite small.

Once the air cells are activated, the exemplary frameless, compliant brace is instantly transformed into a brace having substantially rigid support for the joint. Thus, the device having feedback characteristics provides the necessary support to prevent injury, only when such support is actually required.

Referring again to the variation illustrated in FIG. 11, the same procedure may be applied to provide electrical stimulation to the user once a potentially injurious orientation is detected. Of course, the processor sends signals to the electrical stimuli instead of a compressed air charge. In this configuration, the electrical stimulation acts as a warning system that may be utilized to condition the user in proper joint orientations to prevent injuries. The inclusion of a device having feedback characteristics in a physical therapy regimen will allow practitioners to train patients, through conditioning, in the proper orientations of the joints to avoid potential injuries.

Additionally, as previously mentioned, the electrical stimuli may be utilized in combination with the air cells. In such a combination, the electrical stimuli may be activated once the detected orientation of the joint is near the extremes of the programmed acceptable ranges, and the air cells may be activated once the detected orientation of the joint is outside of the programmed acceptable ranges, in the manner discussed above.

Further variations and alternate embodiments are described below.

Figure 15:
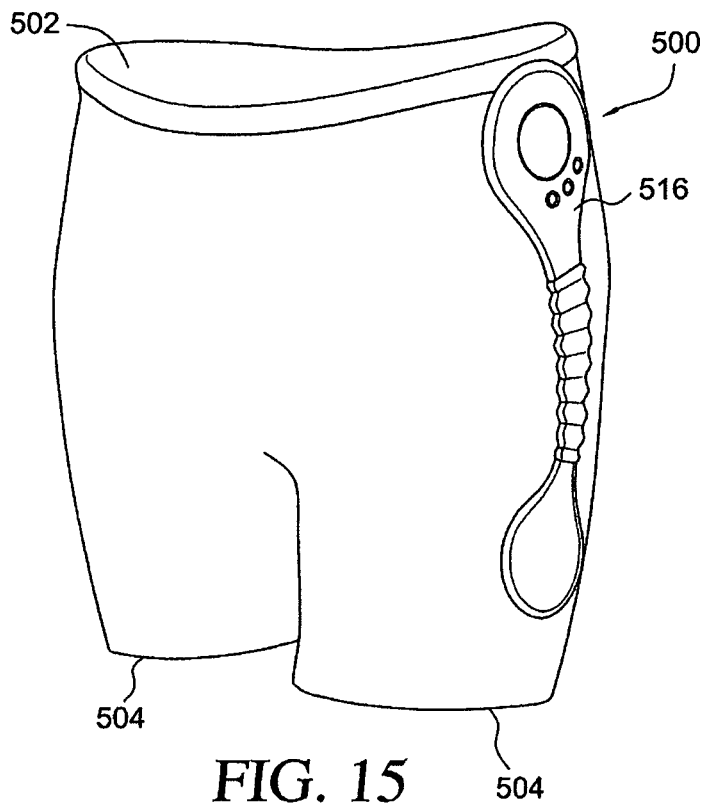
FIG. 15 is a first variation of a device having feedback characteristics in the form of a hip brace.
Figure 16:
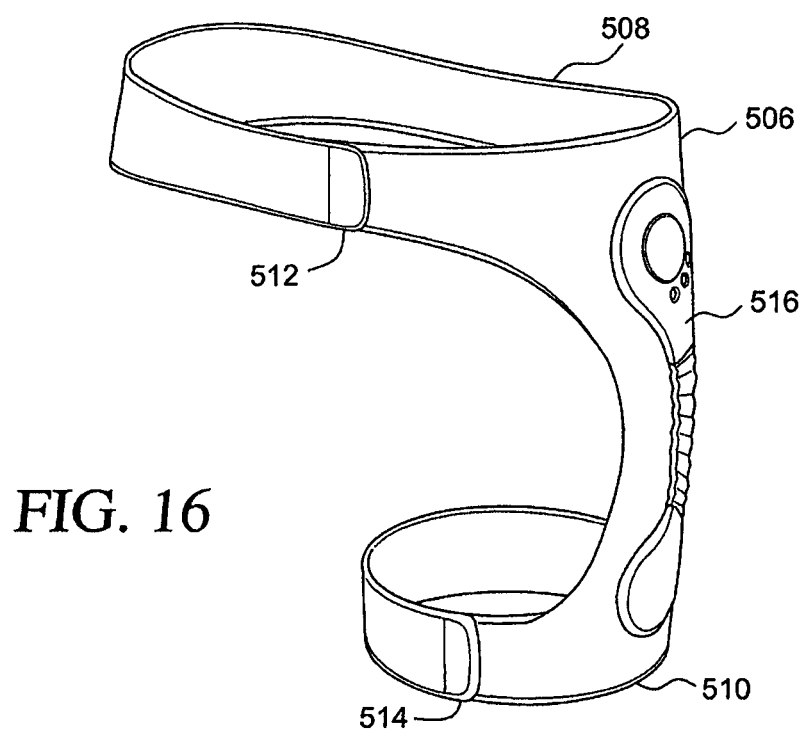
FIG. 16 is a second variation of a device having feedback characteristics in the form of a hip brace.

E. Detailed Description of a Wearable Device Having Feedback Characteristics in the Form of a Hip Brace Two variations of a wearable device having feedback characteristics in the form of a hip brace 500, 506 are respectively shown in FIGS. 15 and 16. The hip braces 500, 506 function in a manner as described above to monitor motions of the hip joint and indicate to a user when range of motion limits are about to be or have been exceeded.

Each of the exemplary hip braces 500, 506 are generally lightweight, low profile, compliant braces formed from suitable materials as described above in relation to the compliant knee braces. The exemplary embodiments of hip braces 500, 506 do not necessarily include bulky support frames, and therefore, are more comfortable to wear. Further, the compliance of the hip braces 500, 506 provides a more conforming fit of the brace to the user, as opposed to rigid support frame type braces, which do not conform to differing body shapes and sizes. Of course, it will be recognized that semi-rigid or rigid supports can be utilized in conjunction with the exemplary hip braces 500, 506 in order to provide more support and stabilization to the anatomy.

The hip brace 500 can be provided as part of an article of clothing, such as, for example, a pair of short pants, and includes a proximal or waist opening 502 and distal leg openings 504. Elastic bands can be provided around the openings 502, 504 in a known manner. Additionally, silicone strips, as discussed above, may be provided around the internal surfaces of the proximal or waist opening 502 and distal leg openings 504 to ensure that the brace 500 is maintained in the proper position on the body. At least one monitoring and control package 516 is positioned along a side of one side of the hip brace 500 to provide monitoring and control for one hip joint. It will be recognized that a second monitoring and control package may be provided along the opposed side of the hip brace 500 to provide monitoring and control for the second hip joint.

The hip brace 506 is similarly constructed, but includes a proximal or waist strap 508 connected along a side portion to a distal or leg strap 510. The proximal strap 508 includes an adjustable strap connector 512 and the distal strap 510 includes an adjustable strap connector 514. The adjustable strap connectors can be constructed in any suitable manner, such as hook and loop connectors, snap fasteners, quick release connectors, hook and eye clasps, or any other suitable mechanism. Additionally, silicone strips, as discussed above, may be provided around the internal surfaces of the proximal and distal straps 508, 510 to ensure that the brace 506 is maintained in the proper position on the body. A monitoring and control package 516 is arranged along the side connecting portion of the brace 506.

Figure 17:
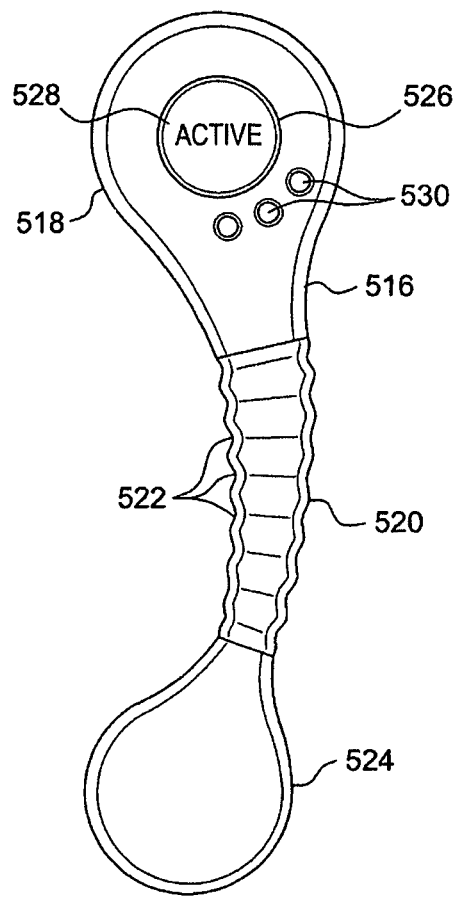
FIG. 17 is a isolated view of the monitoring and control package for use with the variations of the device having feedback characteristics in the form of a hip brace shown in FIGS. 15 and 16.

The monitoring and control package 516, as best seen in FIG. 17, includes a proximal portion 518, a flexible connecting portion 520, and a distal portion 524. It will be recognized that the monitoring and control package 516 need not include the flexible connecting portion 520, for example, in configurations utilizing wireless configurations. The monitoring and control package 516 can be a self contained, integrated package formed of suitable materials, such as plastics and/or metals, that is connected to the braces 500, 506 in any suitable manner, such as by adhesives, ultrasonic welding, heat sealing, sewing, or any other suitable manner. Alternatively, the monitoring and control package 516 can be integrally formed as part of the braces 500, 506, such as by integral molding of the components of the monitoring and control package 516 with the braces 500, 506.

The monitoring and control package 516 includes a flexible connecting portion 520 that connects the proximal portion 518 and the distal portion 524. The flexible connecting portion 520 can include serrations or ridges 522 that enhance the flexibility thereof. The flexible connecting portion 520 may also be formed from a more compliant material than either the proximal portion 518 or distal portion 524. If plastics are used to form the monitoring and control package 516, the proximal portion 518 and distal portion 524 can be formed from a relatively hard or rigid plastic, such as, for example, polyvinylchloride or nylon, and the flexible connecting portion 520 can be formed from a relatively compliant plastic, such as, for example, silicone or ethylene-vinyl-acetate (EVA). Of course, any suitable materials may be utilized.

The flexible connecting portion 520 is sufficiently flexible so that when a user dons the brace 500, 506, the motion of the hip joint and leg is not constrained, or is only slightly constrained, by the resistance to deforming the flexible connecting portion 520.

The monitoring and control package 516 carries a processor, power supply, wired or wireless communications electronics, sensors and appropriate wiring. These components are discussed above in detail with respect to the knee brace. The monitoring and control package 516 also includes a display 526 positioned in the proximal portion 518 (of course, the display 526 may also be positioned in the distal portion 524).

In an exemplary variation of a hip brace 500, 506, a tri-axial accelerometer is positioned in each of the proximal portion 518 and the distal portion 524 of the monitoring and control package 516. Each accelerometer is connected (via wires or wirelessly) to the processor for power and communication therewith in order to monitor the motion of the hip joint and generate signals regarding the motion of the hip joint. If the accelerometers are connected to the processor via wires, such wires can be protectively encased in the material that forms the flexible connecting portion 520.

The signals created by the accelerometers are used by the processor as previously discussed to indicate to a user when predetermined ranges of motion are exceeded or about to be exceeded. It will be recognized that alternative sensors and sensor configurations may be utilized. For example, additional tri-axial accelerometers may be positioned incrementally around the hip braces. Other types of sensors can include the use of multiple single axis or dual axis accelerometers, strain gauges, inclinometers, or any other suitable sensor.

Figure 18:
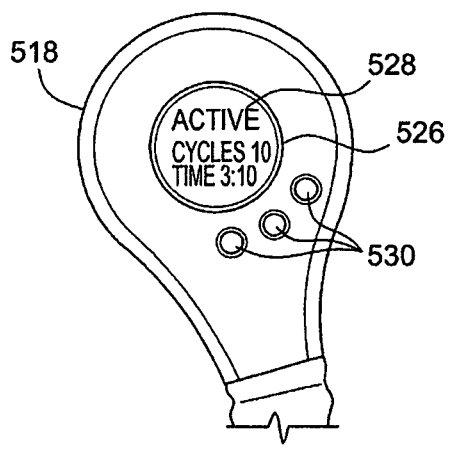
FIG. 18 is a close up partial view of a display of the control package of FIG. 17 indicating an active condition.
Figure 19:
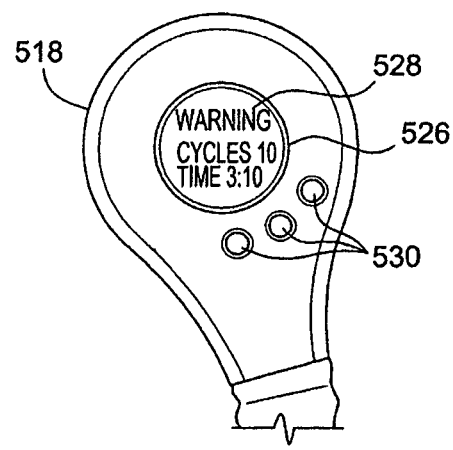
FIG. 19 is a close up partial view of the display of the control package of FIG. 17 indicating a warning condition.

As shown best in FIGS. 18 and 19, the display 526 of the monitoring and control package 516 may be any suitable display that can display indicia 528. For example, the display 526 may be a liquid crystal display (LCD), or may be a display composed of light emitting diodes (LEDs). The display 526 can be utilized to display information (in the form of indicia 528) such as an indication that the device is active, a warning, the number of cycles, and the amount of time the brace has been worn. In this manner, a user can receive immediate feedback regarding the status of the brace.

In addition to the display 526, lights or LEDs 530 are positioned in the proximal portion 518 and can be used to indicate information to a user. For example, the three illustrated LEDs 530 can be utilized to indicate progressively unsafe motions of the hip joint. In other words, when a user begins to approach the limits of an acceptable range of motion, one LED may be lit in a continuous or intermittent manner. As the user gets closer to the limit of an acceptable range of motion, two LEDs may be lit in a continuous or intermittent manner. Finally, when the limit of an acceptable range of notion has been reached or surpassed, all three LEDs can be lit in a continuous or intermittent manner.

In addition to the display 526 and LEDs 530, other suitable alert mechanisms, as discussed in detail above, can be utilized. For example, an audible alert or a tactile alert, such as a vibration, can be used to indicate motions that approach or exceed predetermined allowable ranges of motion.

The allowable ranges of motion can be set and controlled via a remote programming and control module 532, shown in FIGS. 20-26. The remote programming and control module 532 may be, for example, in the form of a personal digital assistant (PDA), cell phone, or any other suitable handheld device that includes integral structure for processing and storing information, such as non-volatile memory. Additional removable memory devices may also be utilized. A housing 534 includes a power button 536, main input control 538, and secondary input controls 540. A display screen portion 542 is utilized to display different menu screens or information screens.

The display screen portion 542 can be any suitable display such as an LCD, a touch-screen LCD, LEDs, or any other suitable display. The remote programming and control module 532 includes appropriate wired or wireless communication structure for communicating with and programming, via wires or wirelessly, the processor of the monitoring and control package 516. The remote programming and control module 532 can also include suitable wired or wireless connections for communicating with personal computers (PCs), the internet, or available cell phone networks.

Figure 20:
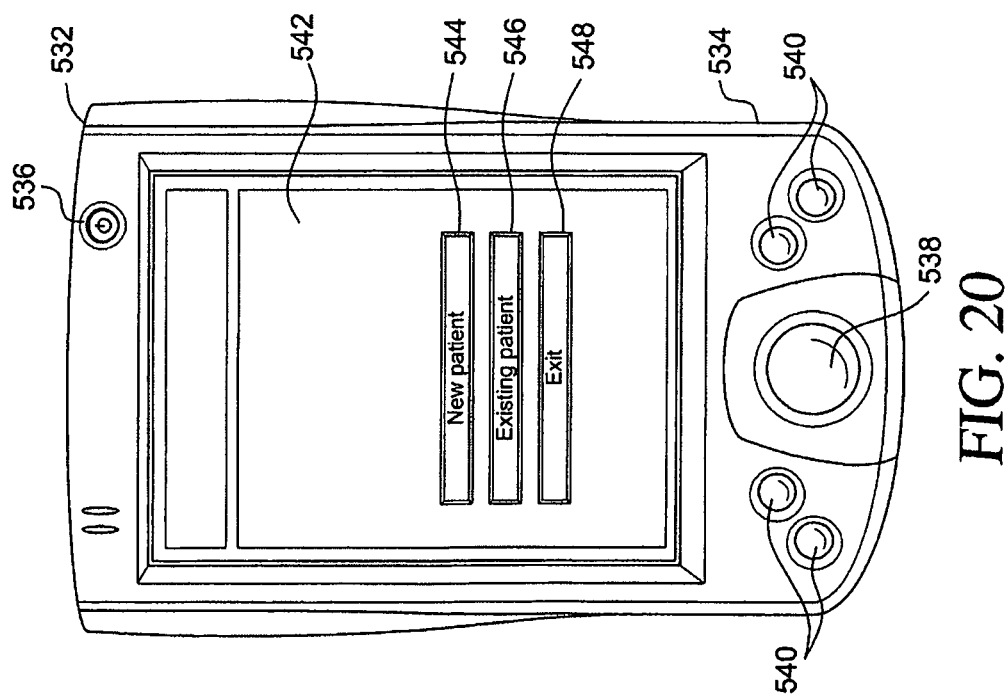

As shown in FIG. 20, the screen 542 displays a welcome screen having the input selections of "new patient" 544, "existing patient" 546, and "exit" 548. This screen can be utilized by a practitioner to begin the process of setting range of motion parameters for a particular brace for a particular patient. A practitioner can select "new patient" 544 to input information and range of motion (ROM) parameters for a new patient or the practitioner can select "existing patient" 546 to alter information and ROM parameters for an existing patient. Selecting "exit" 548 will exit the program.

Figure 21:
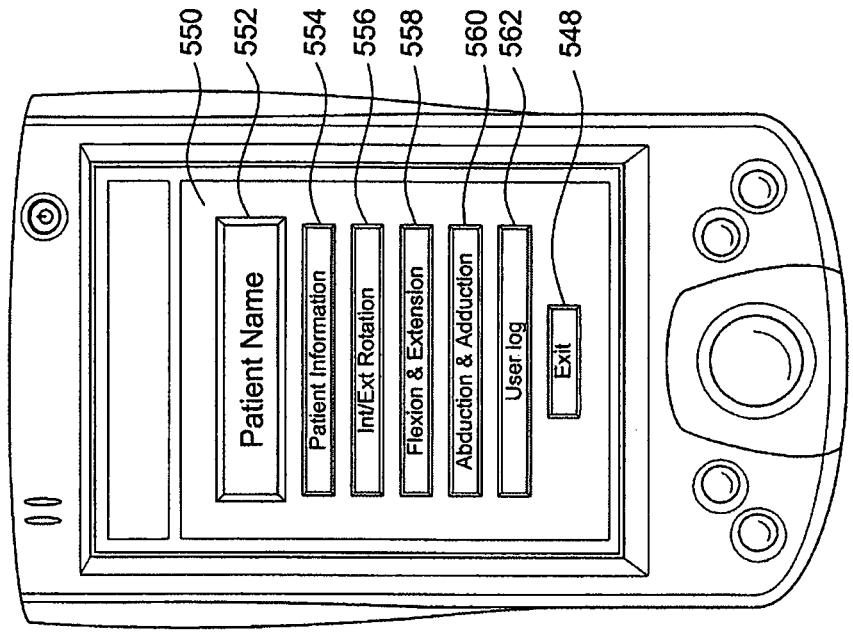

As shown in FIG. 21, a main input screen 550 lists the patient's name 552 and includes the options to input/edit "patient information" 554 and ROM parameters. Additionally, a "user log" 562 may be accessed to allow a practitioner to monitor the brace usage, and whether any of the set ROM parameters were exceeded by the patient. The user log may be encrypted in a known manner so that entries cannot be altered by the patient or user.

In the exemplary embodiment, the practitioner can input ROM parameters for the following motions: "interior and exterior rotation" 556, which is defined by the motion of hip joint (when in flexion or extension) as rotated along a proximal-distal plane towards the medial plane (interior rotation) and away from the medial plane (exterior rotation); "flexion and extension" 558, which is defined by the motion of the hip joint as rotated within the medial-lateral plane; and "abduction and adduction" 560, which is defined by the motion of the hip joint draw away from or towards a position near or parallel to the median axis of the body. As previously discussed, many factors determine the appropriate ranges of motion for a particular patient.

Figure 23:
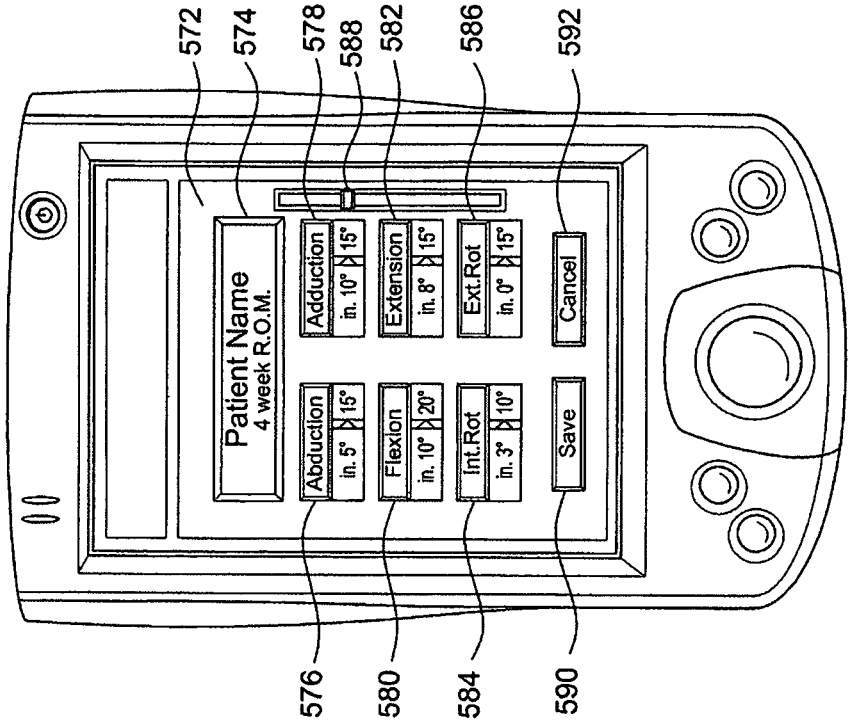
Figure 22:
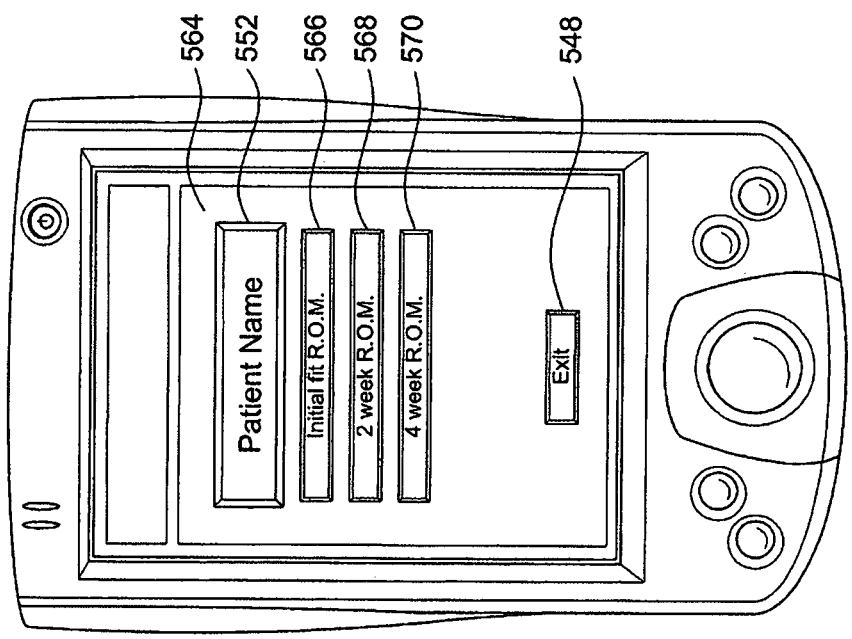

Further, as shown in FIGS. 22 and 23, the ROM parameters can be set to progressively change over given, predefined time periods. For example, as shown in the ROM main screen 564, the ROM parameters can be set for three distinct time periods. First, "initial fit" ROM parameters 566, second, "two week" ROM parameters 568, and third, "four week" ROM parameters 570.

Of course, the time frames can be altered as necessary for particular treatment regimens. For example, a three and six week period may be utilized, or any other suitable or desired time frames.

In use, a practitioner would first select the "initial fit" ROM input 566, and input the ROM parameters, in any suitable manner, such as, for example inputting text and characters, for each of the three motions (listed above) to be measured and/or limited. Next, a practitioner would select either the "two week" or the "four week" ROM inputs 568, 570.

As shown in FIG. 23, once the "four week" ROM input 570 is selected the patient name and ROM time indicator 574 are shown on the ROM input screen 572. As shown, each of the initial ROM parameters is shown for each of the two aspects for each of the three motions (listed above). The initial settings are also shown with the input settings for the specified ROM time frame, in this case the four week ROM. In particular, the following inputs are shown: "abduction initial" and "4 week" setting 576; "adduction initial" and "4 week" setting 578; "flexion initial" and "4 week" setting 580; "extension initial" and "4 week" setting 582; "interior rotation initial" and "4 week" setting 584; and "exterior rotation initial" and "4 week" setting 586. The practitioner can utilize any of the specified inputs, or a graphical slider button 588 in order to input the desired limits for the four week ROM parameters. The practitioner can then save the parameters or cancel the parameters utilizing either the "save" input 590 or the "cancel" input 592.

Once the ROM parameters have been entered by the practitioner, the input screens can be locked from access by the user via password protection or any other suitable encryption. The remote programming and control module 532 can then be given to the patient, along with the brace, for monitoring the motion of the brace.

For example, the physician or practitioner can prescribe an exercise regimen designed to increase flexibility and mobility of the hip joint following an injury or surgery on the hip joint. In order to ensure compliance with the exercise regimen, the patient can utilize the remote programming and control module 532 to monitor the range of motion of their hip while performing the prescribed exercise regimen.

As shown in FIGS. 24-26, three screens may be utilized to show a graphical representation of the ROM of the hip joint in abduction and adduction 594, flexion and extension 596, and interior and exterior rotation 598. While the three screens 594, 596, 598 are shown individually on the remote programming and control module 532, it is contemplated that the three screens can be shown simultaneously. In particular, the three screens may be shown simultaneously on a screen of a PC connected to the remote programming and control module 532.

A graphical representation of the three monitored motions is shown on each of the respective screens 594, 596, 598 to provide a user with an easy reference as to which motion is being monitored. A graphical slider 588 and text box 600 are provided to indicate the extent of motion of the hip joint for each of the two components of the three monitored motions in order to provide the user with an easy manner to determine the actual motion of the hip joint. Additional text boxes 600 can be provided to list the maximum permitted motion range to provide the user with an easy comparison of the actual motion of the hip joint with the prescribed exercise regimen.

When any ROM parameter is approaching or exceeds the maximum allowed ROM parameter, alarms on the brace itself, as discussed above, or on the remote programming and control module 532, can be activated. Exemplary alarms include, but are not limited to, flashing lights or LEDs, and or auditory or tactile alerts.

As previously mentioned, either or both of the processor in the monitoring and control package 516 and the remote programming and control module 532 include memory structure capable of storing data and information on the actual motions of the hip joint. This data may be accessed by a physician or practitioner, over the internet, via a cell phone network, or similar methods, for review and analysis. Similarly, the ROM parameters may be remotely changed by the physician or practitioner to account for unexpected improvements or setbacks.

While these embodiments have been discussed in particular with regard to an exercise regimen, they may of course be utilized for general everyday monitoring of a hip joint following surgery or in order to prevent injury or further injury to a hip joint.

F. Description of Alternate Embodiments and Configurations of a Wearable Device Having Feedback Characteristics While particular embodiments of a wearable device having feedback characteristics are discussed above utilizing selectively inflatable air cells and muscle stimulation, a great variety of mechanisms may be incorporated into a device having feedback characteristics to provide effective warning and protection from injurious orientations of joints. In particular, numerous devices or systems may be implemented to transition a compliant, frameless brace into a substantially rigid brace that provides suitable structural support for the joint.

For example, a brace may be constructed having a compliant sleeve lined with strips of a shape memory material, such as a shape memory polymer, that are also compliant in a particular state of the material. Thus, the strips will be compliant during normal use of the device. Similarly to the procedures noted above, when the processor detects an out of norm or potentially injurious orientation of the joint, the strips of shape memory material may be activated to regain an original substantially rigid shape that closely conforms to the joint to provide structural support thereto.

In a similar variation, strips of a material having a variable stiffness may be utilized. The strips may be compliant in an unactivated state, such that a compliant, frameless brace is created. Again, as previously indicated, if an out of norm or injurious orientation is detected, the strips may be activated such that stiffness of the strips is increased to provide substantially rigid strips that provide structural support to the joint.

In a further variation, a fluid having a variable viscosity may be positioned in one or more cells around a compliant tubular sleeve. The viscosity of the fluid maybe such that in an inactivated state, the sleeve as a whole is a compliant frameless brace that allows suitable freedom of movement of the joint In the manner as previously detailed, the viscosity of the fluid may be increased when an out of norm or injurious orientation is detected. Thus, the brace may be transformed into a brace having a substantially rigid portion providing structural support to the joint when such support is needed. Examples of such fluids that may be suitable for a device having feedback characteristics are discussed in U.S. Pat. No. 7,101,487, granted Sep. 5, 2006, and herein incorporated by reference.

As an alternative, or in addition to the previously discussed feedback or response elements, a feedback or response element that provides a stimulus to the user may be used. As noted in detail above, electrical stimulation of the muscles may be utilized. Such a stimulus may be utilized in physical therapy or exercise regimens to condition the muscles of a user, and the user herself in the proper orientations to maintain the joint in order to prevent injuries.

In alternative embodiments, the processor determines whether or when to activate the feedback or response element to provide a warning stimulus to the user. Such a warning stimulus may be activated at any suitable time in a manner as discussed in detail with respect to the disclosed embodiment, such as when the orientation of the joint approaches the extremes of the predefined limits of a range of suitable orientations. Such a warning stimulus may act as a conditioning stimulus, to which a user may be conditioned to avoid in order to maintain the joint in phase, or otherwise in orientations to avoid injuries to the joint.

An exemplary stimulus may be an audible sound created by a buzzer, a beeper, or other noise generator. Such a sound may be utilized to warn the user that the joint is in an unsafe orientation and that care should be taken to prevent an injury to the joint.

An alternative stimulus could be an indicating lamp or LED (light emitting diode) that is either continuously or intermittently activated to draw attention to the user that an unsafe orientation of the joint has been reached. Such a visible indicator may be placed directly on the device having feedback characteristics or may be spaced from the device, for example on a wrist band, to be more visible to the user.

Other warning stimuli may include an electric shock or pulse that is transmitted to the user in some manner. Such a shock or pulse may be transmitted to the areas around the joint, or may be transmitted to another area of the body that may be more sensitive to such a stimulus.

Another viable warning stimulus may be a vibration that is activated and felt by the user when an unsafe condition of the joint exists. Such a vibration may be generated using small motors with eccentric weights utilizing technology similar to vibrating alerts for mobile or cellular telephones. Again, the vibration may be transmitted to the area directly around the joint or to another part of the body.

A further variation may also include providing a thermal gradient to the user to indicate an unsafe condition of the joint. Such a gradient may be generated utilizing Peltier elements, resistive wires, or other suitable techniques.

Other variations of feedback or response elements and stimuli are contemplated. Further, multiple elements and stimuli may be used in combinations to provide the user with multiple protection and indication. For example, selectively inflatable air cells and variable viscosity fluid may be utilized together to provide structural support to the joint when activated. Audible and visual alarms may be used together to ensure that the user is aware of an unsafe joint orientation. It is noted that many other combinations and configurations may be utilized.

Further, as indicated above, the device having feedback characteristics may be utilized to condition amputees to more effectively integrate a prosthetic device by using more effective biomechanical motions. Thus, the device having feedback characteristics may be incorporated, for example, into a prosthetic foot, knee, and/or leg to help train the amputee in effective biomechanical motions to achieve a more natural dynamic gait. Alternatively, the device having feedback characteristics may be incorporated into a garment, such as a pair of pants. The device having feedback characteristics will function much as described above to alert the user of improper orientations or motions that adversely affect the gait pattern. A processor can be programmed and reprogrammed with suitable ranges and threshold levels for activating a feedback or response mechanism, such as an instant response stimulus. In this manner, the user can be conditioned to use proper biomechanical motions.

In other variations, a device having feedback characteristics may utilize at least one rigid, semi-rigid, or flexible frame member or element to provide additional stabilization to a joint. Such frame members may be in the form of a strip extending axially along the proximal and distal directions of the joint. The use of such additional stabilization is contemplated for weakened joints that are more highly susceptible to injury with very minute variations in joint orientation.

In an exemplary configuration, semi-rigid or flexible strips may be added to pockets along the lateral and medial sides of a tubular brace incorporating the above noted teachings. Alternatively, substantially rigid strips, which may include hinges for rotation, may be added along the lateral and medial sides.

Further configurations may utilize a rigid, semi-rigid, or flexible frame system without a compliant sleeve. In such a configuration, the feedback or response elements and associated sensors and processor may be directly attached to the frame system in a suitable manner.

It is noted that many other variations and configurations of braces and rigid, semi-rigid, or flexible frame systems may be utilized.

G. Conclusion

The disclosed embodiments of a wearable device having feedback characteristics provide an improved protective brace that is lightweight and has a lower profile than a typical brace having a rigid frame, but that provides similar structural support and protection to the joint, only when such support is necessary. The disclosed embodiments further provide a device having feedback characteristics that may be utilized to train or condition the user and/or their muscles to maintain the joint in a proper orientation to avoid injury, or to condition an amputee to use more effective biomechanical motions.

It is understood that the size of the wearable device having feedback characteristics and the components thereof can be adjusted so that different users having different sized joints and body parts may benefit from the present design.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various features from different embodiments. In addition to the variations described herein, other known equivalents for each feature can be mixed and matched by one of ordinary skill in this at to construct a device having feedback characteristics in accordance with principles of the present invention.

Although this invention has been disclosed in the context of certain exemplary embodiments and examples, it therefore will be understood by those skilled in the art that the present invention extends beyond the specifically disclosed embodiments to other alternative embodiments and/or uses of the invention and obvious modifications and equivalents thereof Thus, it is intended that the scope of the present invention herein disclosed should not be limited by the particular disclosed embodiments described above.

The invention claimed is:

1. A wearable device having feedback characteristics comprising:
   a compliant article arranged to extend over an anatomical portion of a wearer, the compliant article comprising a non-rigid material portion having a surface configured to conform to an anatomy across a joint of the wearer;
   a monitoring and control package having a proximal portion connected to a distal portion via a flexible connecting portion and arranged along the non-rigid material portion of the compliant article;
   at least one sensor member arranged on or within the monitoring and control package and configured to detect at least a joint angle of the wearer; and
   at least one feedback element arranged on or within the monitoring and control package and having a first configuration and a second, activated configuration;
   wherein, the first configuration is compliant and the activated configuration provides increased rigidity to prevent undesired orientations of the joint;
   wherein, the feedback element remains in the first configuration when the detected joint angle is within predefined limits; and
   wherein, the feedback element achieves the activated configuration when the detected joint angle is outside of the predefined limits to prevent injury related to joint movement beyond said predefined limits.

2. The device according to claim 1, wherein the at least one sensor member comprises an accelerometer and/or an inclinometer.

3. The device according to claim 1, wherein the flexible connecting portion includes serrated ridges to enhance flexibility.

4. The device according to claim 1, wherein the at least one sensor member comprises two sensor members respectively positioned in the proximal and distal portions of the monitoring and control package.

5. The device according to claim 1, wherein the monitoring and control package includes a processor for analyzing signals provided by the at least one sensor member and for controlling the at least one feedback element.

6. The device according to claim 5, further comprising a remote programming and control module configured to communicate with and program the processor of the monitoring and control package.

7. The device according to claim 6, wherein the detected joint angle is compared with at least one range of motion of the joint angle and the remote programming and control module programs the processor of the monitoring and control package with range of motion limits that progress over a given time period.

8. The device according to claim 6, wherein an additional feedback element is at least one graphical display shown on a screen of the remote programming and control module.

9. The device according to claim 8, wherein the at least one graphical display includes a graphical representation of the at least one range of motion and a textual display indicating the range of motion.

10. The device according to claim 1, wherein the at least one feedback element comprises a display positioned on the monitoring and control package.

11. The device according to claim 1, wherein the at least one feedback element comprises a light emitting diode positioned on the monitoring and control package.

12. The device according to claim 1, wherein the activated configuration of the at least one feedback element is rigid.

13. The device according to claim 1, wherein the at least one feedback element comprises an audible alarm positioned in the monitoring and control package.

14. The device according to claim 1, wherein the at least one feedback element comprises a vibratory alert positioned in the monitoring and control package.

15. The device according to claim 1, wherein the compliant article forms part of an article of clothing.

16. The device according to claim 1, wherein the compliant article comprises a lateral side portion, and the compliant article includes a proximal strap connected along the lateral side portion to a distal strap.

17. The device according to claim 16, wherein the proximal strap and the distal strap are adjustable.

18. The device according to claim 1, wherein the sensor member is configured to detect a change of angle of 5 degrees.

19. The device according to claim 1, wherein the predefined limits are a range of motion, and the monitoring and control package is configured to allow a user to adjust said range of motion.

20. The device according to claim 1, wherein the sensor member is configured to detect the joint angle of the wearer about multiple axes of rotation.

21. The device according to claim 20, wherein the joint angle is a hip angle and the multiple axes correspond to at least two of interior and exterior rotation, flexion and extension, and abduction and adduction.

22. The device according to claim 1, wherein the monitoring and control package can be locked from access by the wearer.

23. A wearable device having feedback comprising:
a compliant article including a proximal strap connected along a first side portion, comprising a non-rigid material configured to conform to an anatomy along a joint of a wearer, to a distal strap, and is arranged to extend over an anatomical portion of the wearer;
a monitoring and control package having a proximal portion connected to a distal portion via a flexible connecting portion, and arranged along the first side portion of the compliant article;
at least one sensor member arranged on or within the proximal or distal portion of the monitoring and control package and configured to detect at least a joint angle of the wearer; and
at least one feedback element arranged on or within the proximal portion of the monitoring and control package and having a first configuration and a second, activated configuration;
wherein, the first configuration is compliant and the activated configuration provides increased rigidity to prevent undesired orientations of the joint;
wherein, the feedback element remains in the first configuration when the detected joint angle is within predefined limits; and
wherein, the feedback element achieves the activated configuration when the detected joint angle is outside of the predefined limits.

24. The device according to claim 23, wherein the sensor member is configured to detect a change of angle of 5 degrees and the activated configuration is rigid.

25. The device according to claim 23, wherein the predefined limits are a range of motion, and the monitoring and control package is configured to allow a user to adjust said range of motion.

26. The device according to claim 23, wherein the sensor member is configured to detect the joint angle of the wearer about multiple axes of rotation.

27. The device according to claim 26, wherein the joint angle is a hip angle and the multiple axes correspond to at least two of interior and exterior rotation, flexion and extension, and abduction and adduction.

28. The device according to claim 23, wherein the monitoring and control package can be locked from access by the wearer.

* * * * *